US009301999B2

(12) United States Patent
Staats et al.

(10) Patent No.: US 9,301,999 B2
(45) Date of Patent: Apr. 5, 2016

(54) PEPTIDE, ADJUVANTS, VACCINES, AND METHODS OF USE

(75) Inventors: Herman F. Staats, Cedar Grove, NC (US); Soman N. Abraham, Chapel Hill, NC (US); Salvatore Pizzo, Bahama, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/498,258

(22) PCT Filed: Sep. 28, 2010

(86) PCT No.: PCT/US2010/050560
§ 371 (c)(1),
(2), (4) Date: Apr. 20, 2012

(87) PCT Pub. No.: WO2011/038397
PCT Pub. Date: Mar. 31, 2011

(65) Prior Publication Data
US 2012/0201782 A1    Aug. 9, 2012

Related U.S. Application Data

(60) Provisional application No. 61/246,228, filed on Sep. 28, 2009.

(51) Int. Cl.
| A61K 38/00 | (2006.01) |
| A61K 38/04 | (2006.01) |
| A61K 39/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| A61K 39/39 | (2006.01) |
| A61K 39/07 | (2006.01) |
| A61K 39/12 | (2006.01) |
| A61K 39/08 | (2006.01) |

(52) U.S. Cl.
CPC .............. *A61K 39/39* (2013.01); *A61K 39/07* (2013.01); *A61K 39/08* (2013.01); *A61K 39/12* (2013.01); *A61K 2039/543* (2013.01); *A61K 2039/55516* (2013.01); *A61K 2039/55527* (2013.01); *A61K 2039/55544* (2013.01); *A61K 2039/55561* (2013.01); *A61K 2039/55572* (2013.01); *C12N 2770/24111* (2013.01); *C12N 2770/24134* (2013.01)

(58) Field of Classification Search
None
See application file for complete search history.

(56) References Cited

U.S. PATENT DOCUMENTS

| 5,589,568 | A | * | 12/1996 | Higashijima et al. | 530/324 |
| 6,849,714 | B1 | * | 2/2005 | Bridon et al. | 530/335 |
| 6,887,470 | B1 | * | 5/2005 | Bridon et al. | 424/133.1 |
| 7,256,253 | B2 | * | 8/2007 | Bridon et al. | 530/300 |
| 2002/0041898 | A1 | | 4/2002 | Unger et al. | |
| 2005/0031630 | A1 | | 2/2005 | Pizzo et al. | |
| 2006/0210551 | A1 | | 9/2006 | Lindsberg et al. | |
| 2006/0276455 | A1 | | 12/2006 | Lindsberg et al. | |
| 2008/0311138 | A1 | | 12/2008 | De Magistris | |
| 2009/0053263 | A1 | | 2/2009 | Cunningham et al. | |
| 2009/0176713 | A1 | | 7/2009 | Tymianski et al. | |
| 2009/0227768 | A1 | | 9/2009 | Eisenberg et al. | |
| 2011/0250130 | A1 | | 10/2011 | Benatuil | |
| 2015/0038530 | A1 | | 2/2015 | Abraham et al. | |

FOREIGN PATENT DOCUMENTS

| EP | 502718 | * | 9/1992 | ............. A01N 37/46 |
| WO | WO 93/03749 | * | 3/1993 | ............. A61K 37/02 |
| WO | WO 2004/101737 | | 11/2004 | |
| WO | WO 2009/033719 | | 3/2009 | |
| WO | 2013148366 | | 10/2013 | |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Skolnick et al. 'From genes to protein structuree and function: novel applications of computational approaches in the genomic era.' Trends in Biotech. 18:34-39, 2000.*
Metzler et al. 'Solution structure of human CTLA-4 and delineation of a CD80/CD86 binding site conserved in CD28.' Nature Structural Biol. 4:527-531, 1997.*
Kuby et al. 'Immunology.' Fourth Edition, Chapter 18: 449-465, 2000.*
Pfeiffer et al. 'The Peptide Mastoparan Is a Potent Facilitator of the Mitochondrial Permeability Transition.' J. Biol. Chem. 270:4923-4932, 1995.*
De Filette et al. 'Recent progress in West Nile virus diagnosis and vaccination.' Veterinary Research 43:1-16, 2012.*
Abraham, S.N. et al., "Mast cell-orchestrated immunity to pathogens," Nat. Rev. Immunol. (2010) 10(6):440-452.
Burlina, A.P. et al., "Mast cells contain large quantities of secretagogue-sensitive N-acetylaspartate," J. Neurochem. (1997) 69:1314-1317.
Ferry, X. et al., "G protein-dependent activation of mast cell by peptides and basic secretagogues," Peptides (2002) 23:1507-1515.
Guo, Y.B. et al., "Effect of mastoparan-1 on lipopolysaccharide-induced acute hepatic injury in mice," Zhonghua Shao Shang Za Zhi (2009) 25(1):53-56 Abstract only.

(Continued)

*Primary Examiner* — Nora Rooney
(74) *Attorney, Agent, or Firm* — Michael Best & Friedrich LLP

(57) ABSTRACT

Provided herein are peptides that have activity as mast cell activating proteins (MCAP), as well as compositions, adjuvant compositions, vaccines, and pharmaceutical formulations that include the peptides. Also provided are methods of using the peptides, including methods for eliciting an immune response to an immunogen in a mammal upon administration.

10 Claims, 6 Drawing Sheets

(56) References Cited

OTHER PUBLICATIONS

Gupta, B. et al., "Intracellular delivery of large molecules and small particles by cell-penetrating proteins and peptides," Adv. Drug Del. Rev. (2005) 57:637-651.
Hirata, Y. et al., "Identification of a 97-kDa mastoparan-binding protein involving in Ca2+ release from skeletal muscle sarcoplasmic reticulum," Mol. Pharmacol. (2000) 57:1235-1242.
International Search Report and Written Opinion for Application No. PCT/US2010/50560 dated Mar. 28, 2011 (16 pages).
Kalesnikoff, J. et al., "New developments in mast cell biology," Nat. Immunol. (2008) 9(11):1215-1223.
Larsen, J.C., "U.S. Army botulinum neurotoxin (BoNT) medical therapeutics research program: past accomplishments and future directions," Drug Dev. Res. (2009) 70:266-278.
Lentschat, A. et al., "Mastoparan, a G protein agonist peptide, differentially modulates TLR4- and TLR2-mediated signaling in human endothelial cells and murine macrophages," J. Immunol. (2005) 174:4252-4261.
McGowen, A.L. et al., "The mast cell activator compound 48/80 is safe and effective when used as an adjuvant for intradermal immunization with Bacillus anthracis protective antigen," Vaccine (2007) 27(27):3544-3552.
McLaughlan, J.B. et al., "Mast cell activators: a new class of highly effective vaccine adjuvants," Nature Med. (2008) 14(5):536-541.
Pulendran, B. et al., "A shot in the arm for mast cells," Nature Med. (2008) 14(5):489-490.
Shelburne, C. et al., "Development of a novel anti-FimH vaccine using a mast cell activator as the adjuvant," J. Immunol (2010) 184 Meeting Abstract Supplement 94:1.
Zhang, P. et al., "A targeted therapeutic rescues botulinum toxin-A poisoned neurons," Nature (2008) 23 pages.
Bois, P. et al., "Mast cells and histamine concentration in muscle and liver of dystrophic mice," (1964) Am. J. Physiol. 206:338-340.
Brown et al., "A dominant role for Fc RII in antibody-enhanced dengue virus infection of human mast cells and associated CCL5 release," Journal of Leukocyte Biology, vol. 80, Dec. 2006, pp. 1242-1250.
Brown et al., "Dengue Virus Infection of Mast Cells Triggers Endothelial Cell Activation," Journal of Virology, Jan. 2011, p. 1145-1150.
Brown et al., "Dramatic caspase-dependent apoptosis in antibody-enhanced dengue virus infection of human mast cells," Journal of Leukocyte Biology, vol. 85, Jan. 2009, pp. 71-80.
Busse, W.W. et al., "Leukotriene pathway inhibitors in asthma and chronic obstructive pulmonary disease," (1999) Clin. Exp. Allergy 29 Suppl 2:110-115.
Fink, J. et al., "Host Gene Expression Profiling of Dengue Virus Infection in Cell Lines and Patients," (2007) PLos Negl Trop Dis 1:e86.
Furuta et al., "Association of mast cell-derived VEGF and proteases in Dengue shock syndrom," PLoS: Neglected Tropical Diseases, vol. 6, Issue 2, Feb. 2012, (12 pages).
Grimbaldestron, M.A. et al., "Mast Cell-Deficient W-sash c-kit Mutant KitW-sh/W-sh Mice as a Model for Investigating Mast Cell Biology in Vivo," (2005) Am. J. Pathol. 167:835-848.
Halstead, "Dengue," Lancet (2007); 370: 1644-1652.
He, S. et al., "The induction of a prolonged increase in microvascular permeability by human mast cell chymase," (1998) Eur. J. Pharmacol. 352:91-98.
King et al., "Dengue Virus Selectively Induces Human Mast Cell Chemokine Production," Journal of Virology, Aug. 2002, p. 8408-8419.
King et al., "Release of Vasoactive Cytokines by Antibody-Enhanced Dengue Virus Infection of a Human Mast Cell/Basophil Line," Journal of Virology, Aug. 2000, p. 7146-7150.
Koda, W. et al., "Evidence of the Participation of Peribiliary Mast Cells in Regulation of the Peribiliary Vascular Plexus Along the Intrahepatic Biliary Tree," (2000) Lab. Invest. 80:1007-1017.
Kunder, C.A. et al., "Mast cell modulation of the vascular and lymphatic endothelium," (2011) Blood 118:5383-5393.
Childs et al., "Effects of Hantaviral Infection on Survival, Growth and Fertility in Wild Rat (Rattus nor vegicus) Populations of Baltimore, Maryland," Journal of Wildlife Diseases, 25(4), 1989. pp. 469-476.
LeDuc, "Epidemiology of Hemorrhagic Fever Viruses," Reviews of Infectious Diseases. vol. II, Supplement, 4, May-Jun. 1989, S730-S735.
Leff, J.A. et al., "Montelukast, a Leukotriene-Receptor Antagonist, for the Treatment of Mild Asthma and Exercise-Induced Bronchoconstriction," (1998) N. Eng. J. Med. 339:147-152.
Low, J.G. et al., "Early Dengue Infection and Outcome Study (EDEN)—Study Design and Preliminary Findings," (2006) Ann Acad Med Singapore 35:783-789.
McClean, S.P. et al., "Refractory cholinergic urticaria successfully treated with ketotifen," (1989) J. Allergy Clin Immunol. 83:738-741.
McFadden, E.R. et al., "Medical Progress. Asthma," (1992) N. Engl. J. Med 327:1928-1937.
PCT/US2013/32553 International Search Report and Written Opinion dated May 29, 2013 (17 pages).
Raut, C.G. et al., "Susceptibility of Laboratory-Bred Rodents to the Experimental Infection With Dengue Virus Type," (1996) Acta. Virol. 40:143-146.
St. John et al., "Immune surveillance by mast cells during dengue infection promotes natural killer (NK) and NKT-cell recruitment and viral clearance," PNAS Early Edition, 2011, 14 pages.
Theoharides, T.C. et al., "Antiallergic Drug Cromolyn May Inhibit Histamine Secretion by Regulating Phosphorylation of a Mast Cell Protein," (1980) Science 207:80-82.
World Health Organization et al., "Dengue, Guidelines for Diagnosis, Treatment, Prevention and Control," 2009, 4 pages.
Zellweger, R.M. et al., "Antibodies enhance infection of LSECs in a model of ADE-induced severe dengue disease," (2010) Cell Host Microbe. 7:128-139.
Brett, J. et al., "Tumor Necrosis Factor/Cachectin Increases Permeability of Endothelial Cell Monolayers by a Mechanism Involviing Regulatory G Proteins," (1989) J. Exp. Med. 169:1977-1991.
Dahlen, S.E. et al., "Leukotrienes promote plasma leakage and leukocyte adhesion in postcapillary venules: In vivo effects with relevance to the acute inflammatory response," (1981) Proc. Natl. Acad. Sci. USA 78:3887-3891).
Finkelman, F.D. et al., "Anaphylaxis: Lessons from mouse models," (2007) J. Allergy Clin. Immunol. 120:506-515.
Flower, R.J., "Inflammatory Effects of Prostaglandin D2 in Rat and Human Skin," (1976) Br. J. Pharmacol. 56:229-233).
Frangogiannis, N.G. et al., "Resident Cardiac Mast Cells Degranulate and Release Preformed TNF-a, Initiating the Cytokine Cascade in Experimental Canine Myocardial Ischemia/Reperfusion," (1998) Circulation 98:699-710.
Huang, C. et al., "The Tryptase, Mouse Mast Cell Protease 7, Exhibits Anticoagulant Activity in Vivo and in Vitro Due to Its Ability to Degrade Fibrinogen in the Presence of the Diverse Array of Protease Inhibitors in Plasma," (1997) J. Biol. Chem. 272:31885-31893.
Koraka, P. et al., "Elevated Levels of Total and Dengue Virus-Specific Immunoglobulin E in Patients With Varying Disease Severity," (2003) J. Med. Viral. 70:91-98.
Mabalirajan, U. et al., "Short Report: TH2 Immune Response in Patients With Dengue During Defervescence: Preliminary Evidence," (2005) Am. J. Trop. Me d. Hyg. 72:783-785.
Oschatz, C. et al., "Mast Cells Increase Vascular Permeability by Heparin-Initiated Bradykinin Formation In Vivo," (2011) Immunity 34:258-268.
Sanchez, L.F. et al., "Degranulation and Histamine Release from Murine Mast Cells Sensitized with Dengue Virus-Immune Sera," (1986) Microbiol. Immunol. 30:753-759.
Sendo, T. et al., "Involvement of proteinase-activated receptor-2 in mast cell tryptase-induced barrier dysfunction in bovine aortic endothelial cells," (2003) Cell Signal. 15:773-781.
Tseng, C.S. et al., "Elevated levels of plasma VEGF in patients with dengue hemorrhagic fever," (2005) FEMS Immunol. Med. Microbiol. 43:99-102.

(56) References Cited

OTHER PUBLICATIONS

Vitarana, T. et al., "Elevated tumour necrosis factor in dengue fever and dengue haemorrhagic fever," (1991) Ceylon Med. J. 36:63-65.
Williams, C.M. et al., "Mast Cells Can Amplify Airway Reactivity and Features of Chronic Inflammation in an Asthma Model in Mice," (2000) J. Exp. Med. 192:455-462.

Atrasheuskaya et al., "Anti-TNF antibody treatment reduces mortality in experimental dengue virus infection," FEMS Immunology and Medical Microbiology 35 (2003) 33-42.
United States Patent Office Final Action for U.S. Appl. No. 14/388,140 dated Jan. 29, 2016 (9 pages).

* cited by examiner

SEQUENCE LISTING

```
<160> NUMBER OF SEQ ID NOS: 72

<210> SEQ ID NO 1
<211> LENGTH: 14
<212> TYPE: PRT
<213> ORGANISM: Artificial Sequence
<220> FEATURE:
<223> OTHER INFORMATION: Sythetic
<220> FEATURE:
<221> NAME/KEY: misc_feature
<222> LOCATION: (1)..(1)
```

```
<223> OTHER INFORMATION: Xaa is I or W
<220> FEATURE:
<221> NAME/KEY: misc_feature
<222> LOCATION: (2)..(2)
<223> OTHER INFORMATION: Xaa is N, Q, or R
<220> FEATURE:
<221> NAME/KEY: misc_feature
<222> LOCATION: (3)..(3)
<223> OTHER INFORMATION: Xaa is L or W
<220> FEATURE:
<221> NAME/KEY: misc_feature
<222> LOCATION: (4)..(4)
<223> OTHER INFORMATION: Xaa is K or R
<220> FEATURE:
<221> NAME/KEY: misc_feature
<222> LOCATION: (5)..(5)
<223> OTHER INFORMATION: Xaa is A or W
<220> FEATURE:
<221> NAME/KEY: misc_feature
<222> LOCATION: (6)..(6)
<223> OTHER INFORMATION: Xaa is any amno acid
<220> FEATURE:
<221> NAME/KEY: misc_feature
<222> LOCATION: (7)..(8)
<223> OTHER INFORMATION: Xaa is A or W
<220> FEATURE:
<221> NAME/KEY: misc_feature
<222> LOCATION: (9)..(9)
<223> OTHER INFORMATION: Xaa is L or W
<220> FEATURE:
<221> NAME/KEY: misc_feature
<222> LOCATION: (10)..(10)
<223> OTHER INFORMATION: Xaa is A, V, or W
<220> FEATURE:
<221> NAME/KEY: misc_feature
<222> LOCATION: (11)..(11)
<223> OTHER INFORMATION: Xaa is K or R
<220> FEATURE:
<221> NAME/KEY: misc_feature
<222> LOCATION: (12)..(13)
<223> OTHER INFORMATION: Xaa is any amino acid
<220> FEATURE:
<221> NAME/KEY: misc_feature
<222> LOCATION: (14)..(14)
<223> OTHER INFORMATION: Xaa is L or W
<220> FEATURE:
<221> NAME/KEY: misc_feature
<222> LOCATION: (1)..(1)
<223> OTHER INFORMATION: optional N-terminal acetyl group
<220> FEATURE:
<221> NAME/KEY: misc_feature
<222> LOCATION: (14)..(14)
<223> OTHER INFORMATION: optional C-terminal -OH or NH2 group

<400> SEQUENCE: 1

Xaa Xaa Xaa Xaa Xaa Xaa Xaa Xaa Xaa Xaa Xaa Xaa Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Artificial variants of mastoparan.
<220> FEATURE:
<221> NAME/KEY: misc_feature
<222> LOCATION: (6)..(6)
<223> OTHER INFORMATION: Xaa is W, L, F, or I
<220> FEATURE:
<221> NAME/KEY: misc_feature
<222> LOCATION: (12)..(12)
<223> OTHER INFORMATION: Xaa is W, L, F, Y, M, I, C, A, V, Q, S, R, H,
      N, E, or G
<220> FEATURE:
<221> NAME/KEY: misc_feature
<222> LOCATION: (13)..(13)
<223> OTHER INFORMATION: Xaa is C, L, W, F, or M
```

-continued

```
<220> FEATURE:
<221> NAME/KEY: misc_feature
<222> LOCATION: (1)..(1)
<223> OTHER INFORMATION: optional N-terminal acetyl group
<220> FEATURE:
<221> NAME/KEY: misc_feature
<222> LOCATION: (14)..(14)
<223> OTHER INFORMATION: optional C-terminal -OH or NH2 group

<400> SEQUENCE: 2

Ile Asn Leu Lys Ala Xaa Ala Ala Leu Ala Lys Xaa Xaa Leu
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

Ile Asn Leu Lys Ala Leu Ala Ala Leu Ala Lys Lys Ile Leu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic

<400> SEQUENCE: 4

Ile Asn Leu Lys Ala Leu Ala Ala Leu Ala Lys Ala Leu Leu
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

Ile Asn Leu Lys Ala Lys Ala Ala Leu Ala Lys Lys Leu Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

Ile Asn Leu Lys Ala Leu Ala Ala Leu Ala Lys Phe Ile Leu
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic

<400> SEQUENCE: 7

Ile Asn Leu Lys Ala Leu Ala Ala Leu Ala Lys Met Ile Leu
1               5                   10
```

```
<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Ile Asn Leu Lys Ala Leu Ala Ala Leu Ala Lys Trp Ile Leu
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic

<400> SEQUENCE: 9

Ile Asn Leu Lys Ala Leu Ala Ala Leu Ala Lys Ile Ile Leu
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

Ile Asn Leu Lys Ala Leu Ala Ala Leu Ala Lys Val Ile Leu
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic

<400> SEQUENCE: 11

Ile Asn Leu Lys Ala Leu Ala Ala Leu Ala Lys Leu Ile Leu
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic

<400> SEQUENCE: 12

Ile Asn Leu Lys Ala Leu Ala Ala Leu Ala Lys Ala Ile Leu
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic

<400> SEQUENCE: 13

Ile Asn Leu Lys Ala Leu Ala Ala Leu Ala Lys Pro Ile Leu
1               5                   10
```

```
<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

Ile Asn Leu Lys Ala Leu Ala Ala Leu Ala Lys Asp Ile Leu
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic

<400> SEQUENCE: 15

Ile Asn Leu Lys Ala Leu Ala Ala Leu Ala Lys Glu Ile Leu
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic

<400> SEQUENCE: 16

Ile Asn Leu Lys Ala Leu Ala Ala Leu Ala Lys Cys Ile Leu
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic

<400> SEQUENCE: 17

Ile Asn Leu Lys Ala Leu Ala Ala Leu Ala Lys Asn Ile Leu
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic

<400> SEQUENCE: 18

Ile Asn Leu Lys Ala Leu Ala Ala Leu Ala Lys Gln Ile Leu
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic

<400> SEQUENCE: 19

Ile Asn Leu Lys Ala Leu Ala Ala Leu Ala Lys Thr Ile Leu
1               5                   10

<210> SEQ ID NO 20
```

```
<211> LENGTH: 14
<212> TYPE: PRT
<213> ORGANISM: Artificial Sequence
<220> FEATURE:
<223> OTHER INFORMATION: Synthetic

<400> SEQUENCE: 20

Ile Asn Leu Lys Ala Leu Ala Ala Leu Ala Lys Tyr Ile Leu
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic

<400> SEQUENCE: 21

Ile Asn Leu Lys Ala Leu Ala Ala Leu Ala Lys Ser Ile Leu
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic

<400> SEQUENCE: 22

Ile Asn Leu Lys Ala Leu Ala Ala Leu Ala Lys Gly Ile Leu
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic

<400> SEQUENCE: 23

Ile Asn Leu Lys Ala Leu Ala Ala Leu Ala Lys His Ile Leu
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic

<400> SEQUENCE: 24

Ile Asn Leu Lys Ala Leu Ala Ala Leu Ala Lys Lys Ile Leu
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic

<400> SEQUENCE: 25

Ile Asn Leu Lys Ala Leu Ala Ala Leu Ala Lys Arg Ile Leu
1               5                   10

<210> SEQ ID NO 26
<211> LENGTH: 14
```

```
<212> TYPE: PRT
<213> ORGANISM: Artificial Sequence
<220> FEATURE:
<223> OTHER INFORMATION: Synthetic

<400> SEQUENCE: 26

Ile Asn Leu Lys Ala Leu Ala Ala Leu Ala Lys Lys Phe Leu
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

Ile Asn Leu Lys Ala Leu Ala Ala Leu Ala Lys Lys Met Leu
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic

<400> SEQUENCE: 28

Ile Asn Leu Lys Ala Leu Ala Ala Leu Ala Lys Lys Trp Leu
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic

<400> SEQUENCE: 29

Ile Asn Leu Lys Ala Leu Ala Ala Leu Ala Lys Lys Ile Leu
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

Ile Asn Leu Lys Ala Leu Ala Ala Leu Ala Lys Lys Val Leu
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic

<400> SEQUENCE: 31

Ile Asn Leu Lys Ala Leu Ala Ala Leu Ala Lys Lys Leu Leu
1               5                   10

<210> SEQ ID NO 32
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 32

Ile Asn Leu Lys Ala Leu Ala Ala Leu Ala Lys Lys Ala Leu
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic

<400> SEQUENCE: 33

Ile Asn Leu Lys Ala Leu Ala Ala Leu Ala Lys Lys Pro Leu
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic

<400> SEQUENCE: 34

Ile Asn Leu Lys Ala Leu Ala Ala Leu Ala Lys Lys Asp Leu
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic

<400> SEQUENCE: 35

Ile Asn Leu Lys Ala Leu Ala Ala Leu Ala Lys Lys Glu Leu
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic

<400> SEQUENCE: 36

Ile Asn Leu Lys Ala Leu Ala Ala Leu Ala Lys Lys Cys Leu
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic

<400> SEQUENCE: 37

Ile Asn Leu Lys Ala Leu Ala Ala Leu Ala Lys Lys Asn Leu
1               5                   10

<210> SEQ ID NO 38
<211> LENGTH: 14
<212> TYPE: PRT
<213> ORGANISM: Artificial Sequence
```

```
<220> FEATURE:
<223> OTHER INFORMATION: Synthetic

<400> SEQUENCE: 38

Ile Asn Leu Lys Ala Leu Ala Ala Leu Ala Lys Lys Gln Leu
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic

<400> SEQUENCE: 39

Ile Asn Leu Lys Ala Leu Ala Ala Leu Ala Lys Lys Thr Leu
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic

<400> SEQUENCE: 40

Ile Asn Leu Lys Ala Leu Ala Ala Leu Ala Lys Lys Tyr Leu
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic

<400> SEQUENCE: 41

Ile Asn Leu Lys Ala Leu Ala Ala Leu Ala Lys Lys Ser Leu
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic

<400> SEQUENCE: 42

Ile Asn Leu Lys Ala Leu Ala Ala Leu Ala Lys Lys Gly Leu
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthetic

<400> SEQUENCE: 43

Ile Asn Leu Lys Ala Leu Ala Ala Leu Ala Lys Lys His Leu
1               5                   10

<210> SEQ ID NO 44
<211> LENGTH: 14
<212> TYPE: PRT
<213> ORGANISM: Artificial Sequence
<220> FEATURE:
```

<223> OTHER INFORMATION: Synthetic

<400> SEQUENCE: 44

Ile Asn Leu Lys Ala Leu Ala Ala Leu Ala Lys Lys Lys Leu
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Synthetic

<400> SEQUENCE: 45

Ile Asn Leu Lys Ala Leu Ala Ala Leu Ala Lys Lys Arg Leu
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Synthetic

<400> SEQUENCE: 46

Ile Asn Leu Lys Ala Phe Ala Ala Leu Ala Lys Lys Ile Leu
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Ile Asn Leu Lys Ala Met Ala Ala Leu Ala Lys Lys Ile Leu
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Synthetic

<400> SEQUENCE: 48

Ile Asn Leu Lys Ala Trp Ala Ala Leu Ala Lys Lys Ile Leu
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Synthetic

<400> SEQUENCE: 49

Ile Asn Leu Lys Ala Ile Ala Ala Leu Ala Lys Lys Ile Leu
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic

```
<400> SEQUENCE: 50

Ile Asn Leu Lys Ala Val Ala Ala Leu Ala Lys Lys Ile Leu
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Synthetic

<400> SEQUENCE: 51

Ile Asn Leu Lys Ala Leu Ala Ala Leu Ala Lys Lys Ile Leu
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Synthetic

<400> SEQUENCE: 52

Ile Asn Leu Lys Ala Ala Ala Ala Leu Ala Lys Lys Ile Leu
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Synthetic

<400> SEQUENCE: 53

Ile Asn Leu Lys Ala Pro Ala Ala Leu Ala Lys Lys Ile Leu
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic

<400> SEQUENCE: 54

Ile Asn Leu Lys Ala Asp Ala Ala Leu Ala Lys Lys Ile Leu
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetic

<400> SEQUENCE: 55

Ile Asn Leu Lys Ala Glu Ala Ala Leu Ala Lys Lys Ile Leu
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Synthetic
```

```
<400> SEQUENCE: 56

Ile Asn Leu Lys Ala Cys Ala Ala Leu Ala Lys Lys Ile Leu
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Synthetic

<400> SEQUENCE: 57

Ile Asn Leu Lys Ala Asn Ala Ala Leu Ala Lys Lys Ile Leu
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Synthetic

<400> SEQUENCE: 58

Ile Asn Leu Lys Ala Gln Ala Ala Leu Ala Lys Lys Ile Leu
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Synthetic

<400> SEQUENCE: 59

Ile Asn Leu Lys Ala Thr Ala Ala Leu Ala Lys Lys Ile Leu
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Synthetic

<400> SEQUENCE: 60

Ile Asn Leu Lys Ala Tyr Ala Ala Leu Ala Lys Lys Ile Leu
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic

<400> SEQUENCE: 61

Ile Asn Leu Lys Ala Ser Ala Ala Leu Ala Lys Lys Ile Leu
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Synthetic

<400> SEQUENCE: 62
```

```
Ile Asn Leu Lys Ala Gly Ala Ala Leu Ala Lys Lys Ile Leu
1               5                   10
```

<210> SEQ ID NO 63
<211> LENGTH: 14
<212> TYPE: PRT
<213> ORGANISM: Artificial Sequence
<220> FEATURE:
<223> OTHER INFORMATION: Synthetic

<400> SEQUENCE: 63

```
Ile Asn Leu Lys Ala His Ala Ala Leu Ala Lys Lys Ile Leu
1               5                   10
```

<210> SEQ ID NO 64
<211> LENGTH: 14
<212> TYPE: PRT
<213> ORGANISM: Artificial Sequence
<220> FEATURE:
<223> OTHER INFORMATION: Synthetic

<400> SEQUENCE: 64

```
Ile Asn Leu Lys Ala Lys Ala Ala Leu Ala Lys Lys Ile Leu
1               5                   10
```

<210> SEQ ID NO 65
<211> LENGTH: 14
<212> TYPE: PRT
<213> ORGANISM: Artificial Sequence
<220> FEATURE:
<223> OTHER INFORMATION: Synthetic

<400> SEQUENCE: 65

```
Ile Asn Leu Lys Ala Arg Ala Ala Leu Ala Lys Lys Ile Leu
1               5                   10
```

<210> SEQ ID NO 66
<211> LENGTH: 14
<212> TYPE: PRT
<213> ORGANISM: Artificial Sequence
<220> FEATURE:
<223> OTHER INFORMATION: Synthetic

<400> SEQUENCE: 66

```
Trp Gln Trp Arg Trp Trp Trp Trp Trp Trp Arg Arg Trp Trp
1               5                   10
```

<210> SEQ ID NO 67
<211> LENGTH: 14
<212> TYPE: PRT
<213> ORGANISM: Artificial Sequence
<220> FEATURE:
<223> OTHER INFORMATION: Synthetic

<400> SEQUENCE: 67

```
Trp Arg Trp Arg Trp Trp Trp Trp Trp Trp Arg Arg Trp Trp
1               5                   10
```

<210> SEQ ID NO 68
<211> LENGTH: 14
<212> TYPE: PRT
<213> ORGANISM: Artificial Sequence
<220> FEATURE:
<223> OTHER INFORMATION: Synthetic

<400> SEQUENCE: 68

```
Trp Gln Trp Arg Trp Trp Trp Trp Trp Arg Trp Trp Trp
1               5                   10
```

```
<210> SEQ ID NO 69
<211> LENGTH: 28
<212> TYPE: PRT
<213> ORGANISM: Artificial Sequence
<220> FEATURE:
<223> OTHER INFORMATION: Synthetic

<400> SEQUENCE: 69

Ile Asn Leu Lys Ala Leu Ala Ala Leu Ala Lys Ala Leu Leu Ile Asn
1               5                   10                  15

Leu Lys Ala Leu Ala Ala Leu Ala Lys Ala Leu Leu
            20                  25
```

```
<210> SEQ ID NO 70
<211> LENGTH: 34
<212> TYPE: PRT
<213> ORGANISM: Artificial Sequence
<220> FEATURE:
<223> OTHER INFORMATION: Synthetic

<400> SEQUENCE: 70

Ile Asn Leu Lys Ala Leu Ala Ala Leu Ala Lys Ala Leu Leu Ser Gly
1               5                   10                  15

Gly Arg Gly Gly Ile Asn Leu Lys Ala Leu Ala Ala Leu Ala Lys Ala
            20                  25                  30

Leu Leu
```

```
<210> SEQ ID NO 71
<211> LENGTH: 31
<212> TYPE: PRT
<213> ORGANISM: Artificial Sequence
<220> FEATURE:
<223> OTHER INFORMATION: Synthetic

<400> SEQUENCE: 71

Ile Asn Leu Lys Ala Leu Ala Ala Leu Ala Lys Ala Leu Leu Gly Gly
1               5                   10                  15

Gly Ile Asn Leu Lys Ala Leu Ala Ala Leu Ala Lys Ala Leu Leu
            20                  25                  30
```

```
<210> SEQ ID NO 72
<211> LENGTH: 14
<212> TYPE: PRT
<213> ORGANISM: Artificial Sequence
<220> FEATURE:
<223> OTHER INFORMATION: Synthetic

<400> SEQUENCE: 72

Ile Asn Leu Lys Ala Ile Ala Ala Leu Val Lys Lys Val Leu
1               5                   10
```

PEPTIDE, ADJUVANTS, VACCINES, AND METHODS OF USE

CROSS REFERENCE TO RELATED APPLICATIONS

This application claims priority to and is a national stage filing under 35 U.S.C. 371 of International Patent Application No. PCT/US2010/050560, filed Sep. 28, 2010, which claims the benefit of priority to U.S. Provisional Patent Application Ser. No. 61/246,228, filed Sep. 28, 2009, each of which is hereby incorporated by reference in its entirety.

STATEMENT REGARDING FEDERALLY SPONSORED RESEARCH OR DEVELOPMENT

This invention was made with United States government support under grant 1R21-AI-059591-01A1 awarded by the National Institute of Allergy and Infectious Diseases. The government has certain rights in this invention.

FIELD

The disclosure relates to vaccine development. Moreover, the disclosure provides peptides, compositions comprising the peptides, and the use thereof as adjuvants, as well as providing vaccines and methods of use, such as inducing an immune response in a mammal for therapeutic purposes.

SEQUENCE LISTING

The sequence listing is provided with the filing of the application in electronic form only, and is incorporated herein by reference. The sequence listing file "028193_9103_SeqList.txt" was generated on Sep. 28, 2010 and is 19,964 bytes in size.

BACKGROUND

Adjuvants are compounds added to vaccine formulations to enhance antigen-specific immune responses in vaccine recipients. Modern vaccine development requires safe and effective adjuvants, but the adjuvants now available to vaccine producers pose problems for human use. The best-known adjuvants include alum, Freund's complete, and Freund's incomplete. Though it has a good safety record, alum stimulates weak antibody responses against protein antigens. O'Hagan et al., (2001) *Biomolecular Engineering* 18:69-85. Moreover, alum adjuvants can induce IgE antibody production and may prompt allergic responses in some recipients. Freund's complete adjuvant and its variants demonstrate promising immunostimulation but are not suitable for human use because they cause unacceptable necrosis and tissue damage. Aucouturier et al., (2001) *Vaccine* 19:2666-2671. Freund's incomplete adjuvant, though less toxic, presents similar safety risks.

Mast cells reside at the host's interface with the surrounding environment and carry out specialized immune functions. Mast cells carry abundant, specialized intracellular granules storing many pre-synthesized immune mediators such as TNF-α, histamine, and tryptase that can be rapidly released through a process known as degranulation. Marshall and Bienenstock, (1994) *Curr Opin Immunol* 6:853-9. Because they can undergo repeated cycles of degranulation and regranulation, mast cells are major mediators of immune stimulation and inflammation in the host. For example, mast cells have been implicated in several inflammatory disorders, including asthma, allergy, inflammatory bowel disease and arthritis, and have also been shown to have beneficial effects in promoting bacterial clearance through neutrophil recruitment to sites of bacterial infection. Malaviya et al., (1996) *Nature* 38:77-80; Echtenacher et al., (1996) *Nature* 381:75-7.

Chemical mast cell activators, such as compound 48/80 (C48/80), have been shown to mediate recruitment of immune cells to regional lymph nodes. Koibuchi, et al., (1985) *European J. of Pharm.* 115(2-3):171-177; Stanovnik, et al., (1988) *Agents Actions* 23(3-4):300-303; McLachlan, et al., (2008) *Nat. Med.* 14(5):536. In addition, C48/80 acts as an adjuvant for nasally administered vaccines with efficacy comparable to cholera toxin—the "gold standard" for mucosal vaccine adjuvant activity. McLachlan, et al., (2008) *Nat. Med.* 14(5):536.

Nevertheless, despite its experimental promise, C48/80 faces barriers that likely preclude its use in human vaccines. McLachlan et al., (2008) *Nat. Med.* 14(5):536; McGowen, et al., (2009) *Vaccine* 27(27):3544-3552. For example, C48/80 is a condensation product of N-methyl-p-methoxyphenethylamine with formaldehyde (see, e.g., SIGMA, Cat. # C2313) and represents an uncharacterized mixture of polymer species. Koibuchi, et al., (1985) *European J. of Pharm.* 115(2-3):171-177. The use of C48/80 in humans would likely require the difficult task of identifying the single species mediating adjuvant activity, if such a single species even exists.

Thus, there is a need for improved and alternative mast cell activating compounds, adjuvant compositions, and vaccine compositions that can induce improved immune responses in a mammalian subject.

SUMMARY

In an aspect, the disclosure provides an isolated peptide of Formula I:

(SEQ ID NO: 1)
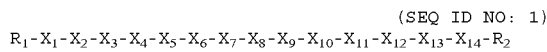

wherein $X_1$ is I or W; $X_2$ is N, Q, or R; $X_3$ is L or W; $X_4$ is K or R; $X_5$ is A or W; $X_6$ is any amino acid; $X_7$ is A or W; $X_8$ is A or W; $X_9$ is L or W; $X_{10}$ is A, V, or W; $X_{11}$ is K or R; $X_{12}$ is any amino acid; $X_{13}$ is any amino acid; $X_{14}$ is L or W; $R_1$ is absent or Ac; and $R_2$ is $NH_2$ or OH.

In an aspect, the disclosure provides An isolated peptide of Formula II:

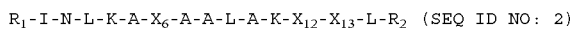
(SEQ ID NO: 2)

wherein $X_6$ is W, L, F, or I; $X_{12}$ is W, L, F, Y, M, I, C, A, V, Q, S, R, H, N, E, or G; $X_{13}$ is C, L, W, F, or M; $R_1$ is absent or Ac; and $R_2$ is $NH_2$ or OH.

In an aspect, the disclosure provides an isolated peptide of any of SEQ ID NOs: 3-72.

In another aspect, the disclosure provides a composition comprising an immunogen in combination with at least one mast cell activating peptide (MCAP) of any of SEQ ID NOs: 1-72.

In another aspect, the disclosure provides an adjuvant composition comprising at least one mast cell activating peptide (MCAP) of any of SEQ ID NOs:1-72 and an optional carrier or vehicle.

In a further aspect, the disclosure provides a pharmaceutical composition comprising an immunogen, at least one mast cell activating peptide (MCAP) of any of SEQ ID NOs:1-72, and a pharmaceutically acceptable carrier.

In another aspect, the disclosure provides a vaccine comprising an immunogen and at least one mast cell activating peptide (MCAP).

In another aspect, the disclosure provides method of inducing an immune response in a mammal comprising concurrently administering an immunogen and at least one mast cell activating peptide (MCAP) in a pharmaceutical carrier.

In a further aspect, the disclosure provides a method of treating a microbial infection in a subject in need thereof comprising administering to the subject, a composition comprising a microbial immunogen and at least one mast cell activating peptide (MCAP) in an amount effective to induce a therapeutic immune response effective to treat the microbial infection.

In an aspect, the disclosure provides a method of treating cancer in a subject in need thereof comprising, administering to the subject, a composition comprising a tumor antigen and at least one mast cell activating peptide (MCAP) in an amount effective to induce a therapeutic immune response effective to treat the cancer.

In another aspect, the disclosure provides a method for eliciting a non-specific immune response in a subject in need thereof comprising, administering to the subject, a composition comprising at least one mast cell activating peptide (MCAP) in an amount effective to induce an innate immune response effective for pathogen clearance.

In another aspect, the disclosure provides a kit for eliciting an immune response to an immunogen, wherein the kit comprises an immunogen, at least one mast cell activating peptide, a delivery device, and instructions for use, wherein the delivery device is capable of administering the immunogen and the at least one mast cell activating protein to a subject.

In other aspects the disclosure provides a medicament comprising at least one MCAP, methods for the preparation of the medicament, and a method comprising administration of the medicament as described herein.

The disclosure provides for additional aspects and embodiments that will be apparent to one of ordinary skill in the art in light of the drawings and detailed description that follows.

DETAILED DESCRIPTION

Figure 1:
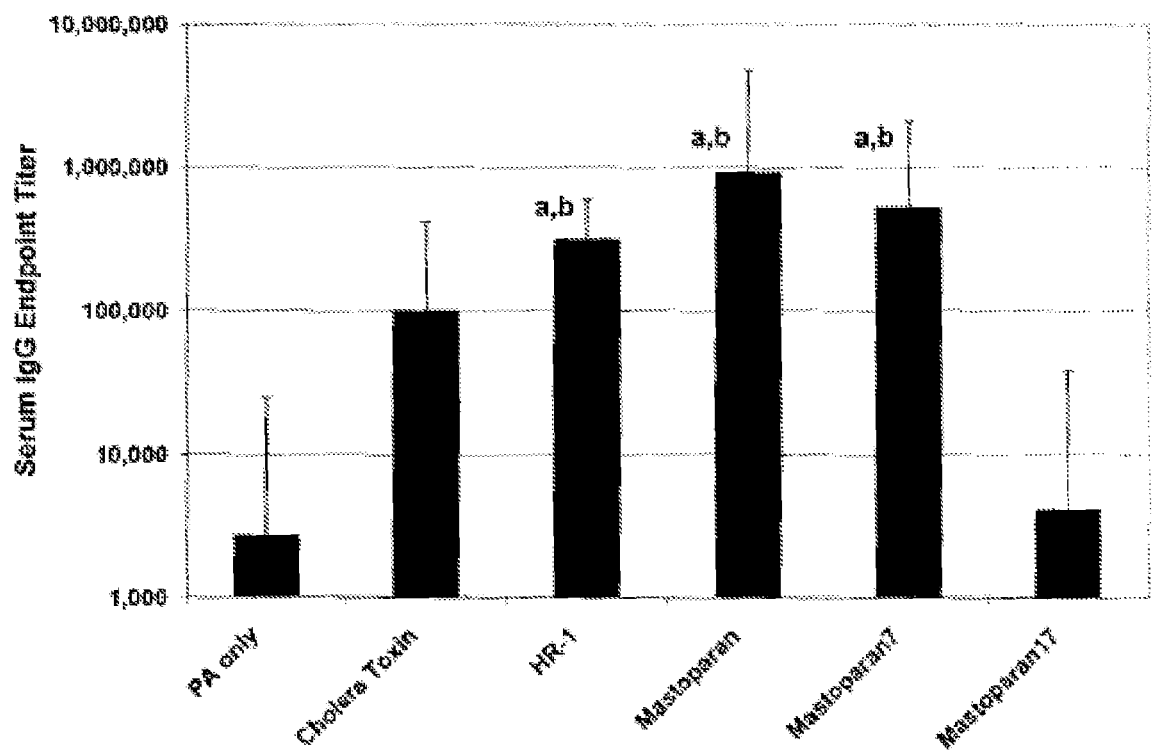
FIG. 1 depicts the mucosal adjuvant activity of MCAP by ELISA assay. C3H/HeN female mice were inoculated with 2.09 μg of recombinant anthrax protective antigen (rPA) alone or in the presence of cholera toxin (CT) (10 μg; positive control adjuvant) or 20 nM of HR-1, Mastoparan (MP), MP7, or MP17 on days 0, 7 and 21. Mastoparan 17 represents an inactive mastoparan analog that is used as a negative control. On day 42, serum samples were collected and tested for the presence of anti-rPA serum IgG by endpoint ELISA. a: significantly greater than PA only; b: significantly greater than mastoparan 17, p=0.05 ANOVA.
Figure 2:
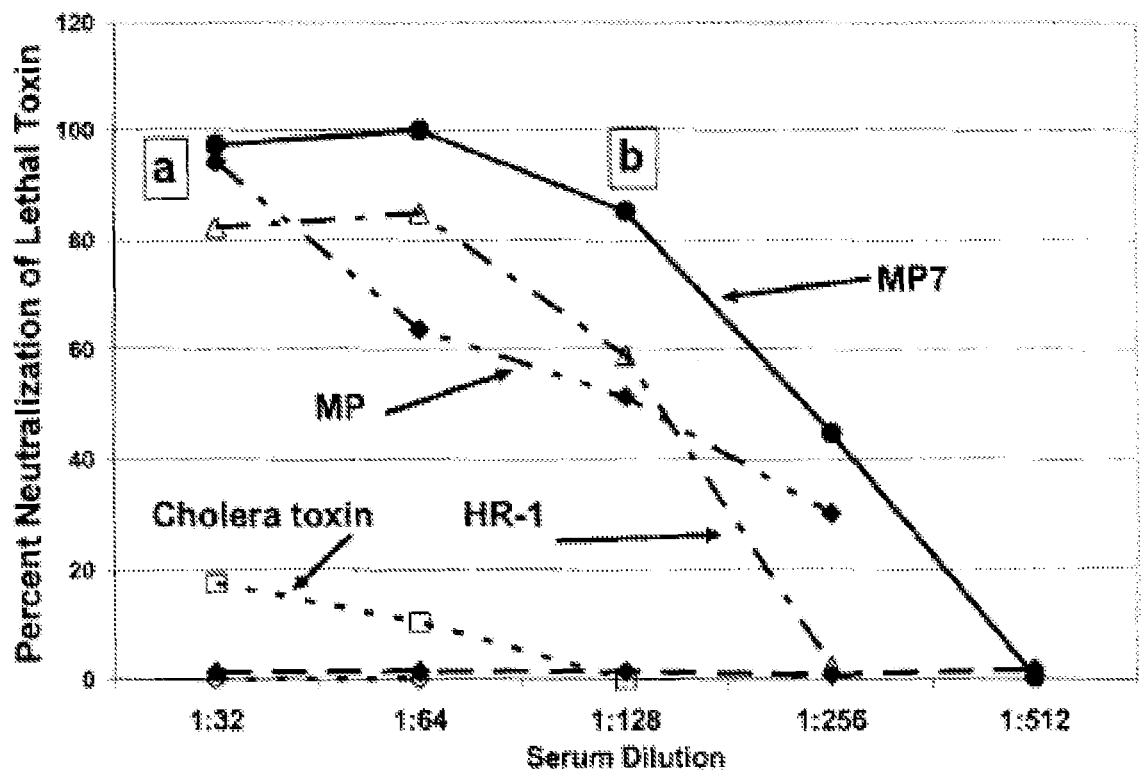
FIG. 2 depicts that MCAP induce lethal toxin neutralizing antibody by macrophage protection assay. Day 42 serum was tested for its ability to neutralize anthrax lethal toxin in a macrophage assay. MP7, MP and HR-1 induced lethal toxin neutralizing antibody responses that were significantly increased versus all other groups at a 1:32 serum dilution (a: p=0.05, ANOVA) and at a 1:128 serum dilution (b: p=0.05 ANOVA).

It will be understood that the various aspects and embodiments described herein are merely intended to provide illustration and do not serve to limit the scope of the claims.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

In a general sense the disclosure relates to peptides, including isolated and/or synthetic peptides that can enhance immune response in a mammal when administered as part of a vaccine composition. The peptides, compositions, vaccine formulations, and methods of use have broad applications as they can provide for a sustained immune response in a subject when combined with any immunogen of interest. The peptides can provide for mast cell activation and therefore are referred to herein as mast cell activating peptides (MCAPs).

Subjects to be treated by the methods and compositions include mammalian subjects, including both human subjects and non-human (animal) subjects such as dogs, cats, rabbits, goats, horses, pigs, cattle, birds (e.g., chickens, turkeys, ducks, geese, quail, pheasant), etc (including both male and female subjects and subjects of all ages including infant, juvenile, adolescent and adult subjects; and for birds subjects in ovo). Subjects may be treated for any purpose, such as for of eliciting a protective immune response; for eliciting the production of antibodies in that subject (typically an animal subject) which antibodies then may be collected and used for other purposes such as diagnostic purposes or administering to other subjects to produce passive immunity therein, etc.

As used herein, the term "antigenic determinant" is any structure that can elicit, facilitate, or be induced to produce an immune response, for example carbohydrate epitopes, lipids, proteins, peptides, or combinations thereof.

As used herein the term "infection" includes the presence of a microbe in or on a subject which, if its growth were inhibited, would result in a benefit to the subject. As such, the term "infection" in addition to referring to the presence of pathogens also includes normal flora which is not desirable, e.g., on the skin of a burn patient or in the gastrointestinal tract of an immunocompromised patient.

A peptide (including an MCAP) as used herein can refer to a compound that can comprise a single amino acid residue. Typically, a peptide comprises a sequence of at least 4 amino acids (amino acid residues) or amino acid mimetics. Embodiments of the disclosure relate to peptides of at least 5, 6, 7, 8, 9, 10, 11, 12, 13, or 14, amino acid residues, mimetics, or combinations thereof. Some embodiments of the aspects described herein provide for peptides of fewer than about 50 amino acid residues and/or mimetics, or fewer than about 25, or fewer about 20 amino acid residues and/or mimetics. The peptides can be provided in a charged form, typically with a net positive charge, and can be generated and used as salts. In some embodiments, the peptides can comprise modifications such as glycosylation, side chain oxidation, or phosphorylation, as long as the modification does not destroy the biological activity of the polypeptides as herein described.

The term "concurrently administered" as used herein means that two compounds are administered sufficiently close in time to achieve a combined immunological effect. Concurrent administration may thus be carried out by sequential administration or simultaneous administration (e.g., simultaneous administration in a common, or the same, carrier).

In various aspects, the disclosure relates to a peptide having adjuvant activity, and including compositions, vaccines, and methods comprising the peptide. Some embodiments provide peptides that are mast cell activating peptides.

As used herein, the term "mast cell activating peptide," "mast cell activating protein," or "MCAP" are generally interchangeable with each other and include any molecule comprising one or a plurality of amino acid residues and can, under appropriate conditions, induce a mast cell to secrete, or induce, mast cell membrane activators. Such peptides include, but are not limited to, polymixin, mastoparans (see, e.g., Kruger, P. G. et al., (2003) *Regul. Pept.* 114(1):29-35; Nakajima, T. et al., (1985) *Peptides* 6 Suppl. 3:425-430; Argiolas, A. et al., (1984) *J. Biol. Chem.* 259(16):10106-10111; de Souza, B. M. et al., (2004) *Rapid Commun. Mass. Spectrom.* 18(10):1095-1102; Konno, K. et al., (2000) *Toxicon.* 38(11):1505-1515; Ziai, M. R. et al., (1990) *Journal of Pharmacy* & Pharmacology 42(7):457-461; Bavec, A. et al., (2004) *J. Peptide Science* 10(11):691-699); peptides derived from the mammalian neuroendocrine protein chromogranin A, such as catestatin (see, e.g., Radek, K. A. et al., (2008) *J. Invest. Dermatol.* 128(6):1525; Kruger, P. G. et al., (2003) *Regul. Pept.* 114(1):29-35); neomycin (Aridor, M. et al., (1993) *Science* 262(5139):1569-1572); and additional molecules capable of binding IgE molecules bound on the mast cell membranes such as IgE-specific antibody or antigen (see, e.g., Mayr, S. et al., (2002) *J. Immunol.* 169(4):2061-2068).

Embodiments of the aspects disclosed herein provide synthetic peptides derived from an MCAP. In an embodiment, the synthetic peptides are derived from mastoparans (i.e. mastoparan analogs) and are optionally isolated and/or purified to a single active species. In some embodiments, the peptide comprises Formula I:

$$R_1-X_1-X_2-X_3-X_4-X_5-X_6-X_7-X_8-X_9-X_{10}-X_{11}-X_{12}-X_{13}-X_{14}-R_2 \text{ (SEQ ID NO: 1)}$$

wherein
$X_1$ is I or W;
$X_2$ is N, Q, or R;
$X_3$ is L or W;
$X_4$ is K or R;
$X_5$ is A or W;
$X_6$ is any amino acid;
$X_7$ is A or W;
$X_8$ is A or W;
$X_9$ is L or W;
$X_{10}$ is A, V, or W;
$X_{11}$ is K or R;
$X_{12}$ is any amino acid;
$X_{13}$ is any amino acid;
$X_{14}$ is L or W;
$R_1$ is absent or Ac; and
$R_2$ is $NH_2$ or OH,
and including salts thereof.

A number of non-limiting examples of peptides of Formula I are disclosed in Tables 1-7. In some further embodiments the peptide comprises Formula II:

$$R_1-I-N-L-K-A-X_6-A-A-L-A-K-X_{12}-X_{13}-L-R_2 \text{ (SEQ ID NO: 2)}$$

wherein
$X_6$ is W, L, F, or I;
$X_{12}$ is W, L, F, Y, M, I, C, A, V, Q, S, R, H, N, E, or G;
$X_{13}$ is C, L, W, F, or M;
$R_1$ is absent or Ac; and
$R_2$ is $NH_2$ or OH.

In some embodiments, the peptide can comprise at least two peptides (e.g., a dimer repeat or multimer repeat) of either SEQ ID NO:1 or SEQ ID NO:2. In such embodiments, the peptide can comprise an optional linker moiety located between and linking the at least two peptides. Any linker moiety known in the art can be used in the embodiments described herein. In some embodiments, the linker moiety comprises any common peptide linker motif. In some embodiments the peptide linker is SGGRGG, GGG, or SGG. In some embodiments the peptide comprises MP7-2X (INLKALAALAKALL-INLKALAALAKALL-NH₂ or —OH), MP7-2Xa (INLKALAALAKALL-SGGRGG-INLKA-LAALAKALL-NH₂ or -OH), or MP7-2XB (INLKA-LAALAKALL-(S/G)GG-INLKALAALAKALL-NH₂ or —OH)

In embodiments, the peptide comprises a sequence of SEQ ID NO:2, wherein $X_6$ is leucine and $X_{12}$ and $X_{13}$ are defined as above. In some embodiments the peptide comprises a sequence of SEQ ID NO:2, wherein $X_6$ is leucine, $X_{13}$ is isoleucine, and $X_{12}$ is defined as above. In some embodiments, $X_6$ is leucine, $X_{13}$ is isoleucine, and $X_{12}$ comprises L, F, Y, W, M, or I.

In some embodiments the peptide is SEQ ID NO:6, SEQ ID NO:7, SEQ ID NO:8, SEQ ID NO:9, SEQ ID NO:11, or SEQ ID NO:20.

In other embodiments, peptides of SEQ ID NO:1 include, but are not limited to, mastoparan (INLKALAALAKKIL-NH₂ or —OH), mastoparan 7 (INLKALAALAKALL-NH₂ or -OH), Duke MCAP C (WQWRWWWWWWRRWW-NH₂ or -OH), Duke MCAP F (WRWRWWWWWWRRWW-NH₂ or —OH), or Duke MCAP I (WQWRWWWWWWR-WWW-NH₂ or —OH).

As used herein, the term "TLR" or "toll-like receptor" refers to a class of proteins that play a role in the innate immune system. These receptors are single membrane-spanning non-catalytic receptors that recognize structurally conserved molecules (e.g., ligands) derived from microbes and the host. Once these microbes have breached physical barriers such as the skin or intestinal tract mucosa, they are recognized by TLRs which activate immune cell responses. The term "TLR ligand" refers to those pathogen-associated molecules that bind the toll-like receptor of immune cells. These molecules are generally critical for the pathogen's function and cannot be eliminated or changed through mutation (i.e., evolutionarily conserved). Such molecules include, but are not limited to, lipopolysaccharides (LPS), lipoproteins, lipopeptides, lipoarabinomannan, proteins such as flagellin from bacterial flagella, double-stranded RNA or viruses or the unmethylated CpG islands of bacterial and viral DNA, MPL, and certain other RNA and DNA.

Immunogens

As noted above, the disclosure provides broad application and use of the MCAPs having adjuvant activity, and thus, can be used in combination with any immunogen of interest. As used herein, the term "immunogen" refers to any substance or organism that provokes an immune response (produces immunity) when introduced into the body. The particular immunogen used (e.g., proteins, peptides, polysaccharides, lipids, and the like, including glycoproteins, glycolipids, glycoproteins, lipoproteins, lipopolysaccharides and the like) is not critical to the invention. Immunogens are known in the art and can be incorporated for use in the methods and compositions provided herein using any common method. Non-limiting lists of suitable immunogens for use in the various aspects and embodiments described herein can be found in the literature, for example, BioCarb Chemicals Catalogue; and The Jordan Report: Accelerated Development of Vaccine 1995 NIH, Bethesda, Md., 1995, both of which are incorporated herein by reference.

In some embodiments an immunogen comprises any immunogen derived from bacteril surface polysaccharides which can be used in carbohydrate-based vaccines. Bacteria typically express carbohydrates on the cell surface as part of glycoproteins, glycoplipids, O-specific side chains of lipopolysaccharides, capsular polysaccharides and the like. Non-limiting examples of suitable bacterial strains include *Streptococcus pneumonia, Neisseria meningitidis, Haemophilus influenza, Klebsiella* spp., *Pseudomonas* spp., *Salmonella* spp., *Shigella* spp., and Group B *streptococci*. In some embodiments any known bacterial carbohydrate epitope (e.g., Sanders, et al. (1995) *Pediatr. Res.* 37:812-819; Bartoloni, et al. (1995) *Vaccine* 13:463-470; Pirofski, et al., (1995) *Infect. Immun.* 63:2906-2911 and International Publication No. WO 93/21948) and are further described in U.S. Pat. No. 6,413,935) can be used as an immunogen in the compositions and methods herein described.

Some embodiments provide for an immunogen that comprises a viral antigen. Non-limiting examples of viral antigens or viral immunogens include those derived from HIV (e.g., gp120, nef, tat, pol) and West Nile Virus (WNV).

Some embodiments provide for an immunogen that comprises a fungal antigen. Non-limiting examples of fungal antigens include those derived from *Candida albicans, Cryptococcus neoformans, Coccidoides* spp., *Histoplasma* spp., and *Aspergillus* spp.

Some embodiments provide for an immunogen that comprises an antigen derived from a parasite. Non-limiting examples of parasitic antigens include those derived from *Plasmodium* spp., *Trypanosoma* spp., *Schistosoma* spp., *Leishmania* spp. and the like.

In some embodiments the immunogen comprises a carbohydrate epitope. Non-limiting examples of carbohydrate epitopes that can be used in the aspects and embodiments described herein include: Galα1,4Galβ (for bacterial vaccines); GalNAcα (for cancer vaccines); Manβ1,2(Manβ)$_n$ Manβ-(for fungal vaccines useful against, for example, *C. albicans*), wherein n is any integer, including zero; Gal-NAcβ1,4(NeuAcα2,3)Galβ1,4Glcβ-O-ceramide (for cancer vaccines); Galα1,2(Tyvα1,3)Manα1,4Rhaα1,3Galα1,2-(Tyα1,3)Manα4Rha- and Galα1,2(Abeα1,3)Manα1,4Rhaα1,3Galα1,2(Abeα1,3) Manα1,4Rhaα1,3Galα1,2(Abeα1,3)Manα1,4Rha (both of which are useful against, for example, *Salmonella* spp.). Description of other exemplary carbohydrate epitopes as antigens or immunogens and the synthesis thereof are described further in U.S. Pat. No. 6,413,935.

In some embodiments, the immunogen can be an anthrax immunogen; i.e. an immunogen that produces protective immunity to *Bacillus anthracis*, such as anthrax vaccine, A, (see, e.g., U.S. Pat. No. 5,728,385; BioThrax® Emergent Biosolutions, Rockville, Md.). Other examples of immunogens or antigens include, but are not limited to, those that produce an immune response or antigenic response to the following diseases and disease-causing agents: adenoviruses; Bordetella pertussus; Botulism; bovine rhinotracheitis; *Branhamella catarrhalis*; canine hepatitis; canine distemper; Chlamydiae; Cholera; coccidiomycosis; cowpox; cytomegalovirus; cytomegalovirus; Dengue fever; dengue toxoplasmosis; Diphtheria; encephalitis; Enterotoxigenic *Escherichia coli*; Epstein Barr virus; equine encephalitis; equine infectious anemia; equine influenza; equine pneumonia; equine rhinovirus; feline leukemia; flavivirus; Globulin; *haemophilus influenza* type b; *Haemophilus influenzae; Haemophilus pertussis; Helicobacter pylori; Hemophilus*; hepatitis; hepatitis A; hepatitis B; Hepatitis C; herpes viruses; HIV; HIV-1 viruses; HIV-2 viruses; HTLV; Influenza; Japanese encephalitis; *Klebsiellae* species; *Legionella pneumophila; leishmania*; leprosy; lyme disease; malaria immunogen; measles; meningitis; meningococcal; Meningococcal Polysaccharide Group A, Meningococcal Polysaccharide Group C; mumps; Mumps Virus; mycobacteria and; *Mycobacterium tuberculosis; Neisseria; Neisseria gonorrhoeae; Neisseria meningitidis*; ovine blue tongue; ovine encephalitis; papilloma; parainfluenza; paramyxovirus; paramyxoviruses; Pertussis; Plague; Pneumococcus; Pneumocystis carinii; Pneumonia; Poliovirus; Proteus species; *Pseudomonas aeruginosa*; rabies; respiratory syncytial virus; rotavirus; Rubella; *Salmonellae*; schistosomiasis; Shigellae; simian immunodeficiency virus; Smallpox; *Staphylococcus aureus; Staphylococcus* species; *Streptococcus pneumoniae; Streptococcus pyogenes; Streptococcus* species; swine influenza; tetanus; *Treponema pallidum*; Typhoid; *Vaccinia*; varicella-zoster virus; and *Vibrio cholerae*. The antigens or immunogens can include various toxoids, viral antigens and/or bacterial antigens such as antigens antigens commonly employed in the following vaccines: chickenpox vaccine; diphtheria, tetanus, and pertussis vaccines; *haemophilus influenzae* type b vaccine (Hib); hepatitis A vaccine; hepatitis B vaccine; influenza vaccine; measles, mumps, and rubella vaccines (MMR); pneumococcal vaccine; polio vaccines; rotavirus vaccine; anthrax vaccines; and tetanus and diphtheria vaccine (Td) (see, e.g., U.S. Pat. No. 6,309,633). The antigens or immunogens can include any type of antigen associated with cancer such as, for example, tumor antigens (including antigens associated with leukemias and lymphomas) and antigens that are associated with agents that can cause cancer (e.g., tumorigenic viruses such as, for example, adenovirus, HBV, HCV, HTLV, Kaposi's sarcoma-associated herpesvirus, HPV (Gardasil®), and the like).

Antigens or immunogens that are used to carry out the present invention include those that are derivatized or modified in some way, such as by conjugating or coupling one or more additional groups thereto to enhance function or achieve additional functions such as targeting or enhanced delivery thereof, including but not limited to those techniques described in U.S. Pat. No. 6,493,402 to Pizzo et al. (α-2 macroglobulin complexes); U.S. Pat. No. 6,309,633; U.S. Pat. No. 6,207,157; U.S. Pat. No. 5,908,629, etc.

Pharmaceutical Compositions and Methods

The peptides, compositions, including pharmaceutical compositions, and vaccine compositions described herein, can be administered to subjects as described above for prophylactic and/or therapeutic purposes. Embodiments of this administration method or use can be used to elicit and/or enhance immune responses against immunogens. Examples of diseases or disorders which can be treated using the present disclosure are described above.

In embodiments relating to therapeutic applications, the administration can be performed on a subject already suffering from the disorder of interest. Those in the incubation phase or the acute phase of the disease can be treated by the methods described herein, either alone or in conjunction with other treatments, as suitably based on the particular disease/condition, patient, and combination. One of skill in the art will be able to determine when a combination treatment is or is not suitable.

In therapeutic methods and uses, the composition described herein can be administered to a patient in an amount sufficient to elicit an effective immune response (e.g., a cellular immune response and/or a humoral immune response) to the antigen and to treat, or at least partially arrest, symptoms and/or complications. An amount adequate to accomplish this is often referred to as "therapeutically effective dose." Amounts effective for this use will depend in part on the antigen composition, the manner of administration, the stage and severity of the disease being treated, the weight and general state of health of the patient, and the judgment of the prescribing physician.

Effective amounts of the compositions and peptides disclosed herein for the initial immunization, that is for therapeutic or prophylactic administration, can range from about 1 μg to about 10,000 μg of immunogen for a 70 kg patient, usually from about 100 to about 8000 μg, and preferably between about 200 and about 6000 μg. These doses may be followed by boosting dosages of from about 1.0 μg to about 1000 μg of immunogen pursuant to a boosting regimen over weeks to months depending upon the patient's response and condition by measuring specific immune responses.

In some embodiments, the methods and compositions described herein can be employed in serious disease states, that is, life-threatening or potentially life threatening situations. In such cases, in view of the minimization of extraneous substances and the relative non-toxic nature of the conjugates, it is possible and may be felt desirable by the treating physician to administer substantial excesses of these compositions.

In further embodiments, the peptides, compositions, and vaccines can be used to stimulate a prophylactic immune response in a subject to prevent, treat, reduce, and/or ameliorate bacterial infections, viral infections, fungal infections, parasitic infections and cancer. Effective amounts are as described above. Additionally, one of ordinary skill in the vaccine arts would also know how to adjust or modify prophylactic treatments, as appropriate, for example by boosting and adjusting dosages and dosing regimes.

Therapeutic administration may begin at the first sign of disease (such as onset of clinical symptoms) or the detection or surgical removal of tumors or shortly after diagnosis in the case of acute infection. This can be followed by boosting doses until symptoms are substantially abated and for a period thereafter. In chronic infection, initial high doses followed by boosting doses may be required.

Treatment of an infected individual with the compositions of the disclosure may hasten resolution of the infection in acutely infected individuals. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

An aspect of the disclosure provides for the treatment of chronic infection through stimulation of the immune system to eliminate virus-infected cells in individuals with latent infections. Embodiments provide an amount of composition in a formulation and mode of administration sufficient to effectively elicit and/or enhance an immune response. Thus, for treatment of chronic infection, a representative dose can be in the range of about 1.0 μg to about 5000 μg, or about 5 μg to 1000 μg for a 70 kg patient per dose. Immunizing doses followed by boosting doses at established intervals, e.g., from one to four weeks, may be required, possibly for a prolonged period of time to effectively immunize an individual. In the case of chronic infection, administration should continue until at least clinical symptoms or laboratory tests indicate that the viral infection has been eliminated or substantially abated and for a period thereafter.

Some embodiments relating to pharmaceutical compositions for therapeutic or prophylactic treatment provide for formulations specific for any of mucosal (oral, nasal, rectal, vaginal, tracheal, etc.), parenteral, topical, or local administration. For purposes herein, mucosal administration is different from topical administration, as mucosal administration refers to application of the vaccine to a mucosal surface such as a surface of the respiratory tract, gastrointestinal tract, reproductive tract, etc. In some embodiments, the pharmaceutical compositions are suitably administered parenterally, e.g., intravenously, subcutaneously, intradermally, or intramuscularly. Topical administration (i.e., non-mucosal) can be to a non-mucosal surface of a subject, such as the eye, ear, nails, hair, or skin, in any appropriate form such as aqueous or non-aqueous liquid (e.g., droplet), emulsion, paste, ointment, cream etc. In some embodiments the administration is as described for the treatment of wounds or scarring as discussed herein. Thus, the disclosure provides compositions for topical (mucosal or non-mucosal) or parenteral administration which comprise a mast cell activation peptide or conjugate thereof, dissolved or suspended in an acceptable carrier, such as an aqueous carrier. In embodiments, the pharmaceutical composition is administered nasally. Any variety of aqueous carriers may be used, e.g., water, buffered water, 0.9% saline, 0.3% glycine, hyaluronic acid and the like. These compositions can be sterilized by conventional, well known sterilization techniques, or may be sterile filtered. The resulting solutions may be packaged for use as is, or lyophilized, the lyophilized preparation being combined with a sterile solution prior to administration. The compositions can contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, sorbitan monolaurate, triethanolamine oleate, etc. Alternatively, the pharmaceutical compositions described herein can also be in dry powder formulations. In embodiments relating to dry powder vaccine formulations, typically the liquid vaccine is rapidly frozen and dried in a vacuum (e.g., freeze-dried) in the presence of at least one bulking agent (such as trehalose or other sugars) to provide a vaccine formulation that has superior temperature stability. Such dry powder vaccine formulations may be administered to the host as a dry powder, thereby eliminating the need for liquid reconstitution.

In aspects described herein that relate to compositions, including pharmaceutical compositions and vaccine compositions, some embodiments provide a composition that comprises an immunogen in combination with at least one mast cell activating peptide (MCAP). In further embodiments the MCAP is a peptide of SEQ ID NO:1 or SEQ ID NO:2. In yet further embodiments the MCAP is a peptide of any of SEQ ID NOs:3-72.

In some embodiments, the disclosure provides a composition that consists essentially of an immunogen in combination with at least one mast cell activating peptide (MCAP). In further embodiments the MCAP is a peptide of SEQ ID NO:1 or SEQ ID NO:2. In yet further embodiments the MCAP is a peptide of any of SEQ ID NOs:3-72.

In another aspect, the disclosure provides a vaccine which comprises a peptide adjuvant and an immunogen. In embodiments, the peptide adjuvant comprises a peptide of Formula I (SEQ ID NO:1) or Formula II (SEQ ID NO:2). Carriers are well known in the art, and include thyroglobulin, albumins such as bovine serum albumin, tetanus toxoid, polyamino acids such as poly(lysine:glutamic acid), hepatitis B virus core protein, hepatitis B virus recombinant vaccine, diphtheria toxin CRM mutant and the like. The vaccines can also contain a physiologically tolerable (acceptable) diluent such as water, phosphate buffered saline, or saline. In addition to the MCAP peptide adjuvants described herein the composition may include an additional adjuvant, such as complete or incomplete Freund's adjuvant, aluminum phosphate, aluminum hydroxide, alum, cytokines (e.g., IL-1α, IL-1β, etc.), TLR ligands, etc. Upon immunization with a composition as described herein, via injection, aerosol, nasal, oral, topical transdermal or other route, the immune system of the host can produce an immune response and/or an enhanced immune response, that can be humoral and/or cellular. In some embodiments the additional adjuvants comprise at least one TLR ligand, (e.g., CpG and MPL).

Vaccine compositions can be administered to a subject, such as a human patient, susceptible to or otherwise at risk of disease, to elicit and/or enhance an immune response against an antigenic determinant. Such an amount can be referred to as an "immunogenically effective dose," either for therapeutic or prophylactic use. In this use, the precise amounts again depend on the patient's state of health and weight, the mode of administration, the nature of the formulation, etc., but generally range from about 1.0 µg to about 5000 µg per 70 kilogram patient, more commonly from about 10 µg to about 500 µg per 70 kg of body weight.

Methods of Activating Immune System to Treat Microbial Infections

The methods and compositions described above can be used in methods for inducing a therapeutic immune response to treat a microbial infection. In some embodiments, the MCAPs, and/or compositions thereof, can be used in concert with an immunogen or antigen to evoke specific immunity against the infecting pathogen. In some embodiments the MCAPS, and/or compositions thereof, can be used in the absence of an immunogen or antigen to evoke non-specific immunity (innate immunity, involving recruitment of neutrophils, NK, or NKT cells for pathogen clearance). Also, as noted above, the disclosure provides methods of treating microbial infections (e.g., bacterial, viral, fungal and protozoal infections) in subjects in need thereof. Examples of microbial infections that may be treated by such methods include but are not limited to Category A and B pathogens as defined by the CDC Biological Diseases/agents list (e.g. Anthrax (*Bacillus anthracis*), Plague (*Yersinia pestis*), Smallpox (Variola major), Tualernia (*Francisella tularensis*) Viral hemorrhagic fevers (e.g. Ebola, Lassa); *Listeria monocytogenes*, yeast infections. Examples also include pathogens that typically cause community as well as hospital acquired infections (Gram negative enterobacteria, *Escherichia coli Staphylococcus aureus, Streptococcus pyogenes*, other gram positive bacteria most fungi and parasites). Examples also include newly emerging pathogens such as SARS, pathogens involved in post operative infections, and pathogens causing localized dermal infections. A particular example is *Salmonella typhimurim*.

Thus in some embodiments microbes that may be treated using the methods disclosed herein include bacteria from the family Enterobacteriaceae. In other embodiments bacteria of a genus selected from the group consisting of *Escherichia, Proteus, Salmonella, Klebsaiella, Providencia, Enterobacter, Burkholderia, Pseudomonas, Acinetobacter, Aeromonas, Haemophilus, Yersinia, Neisseria,* and *Erwinia, Rhodopseudomonas*, or *Burkholderia* may be treated by the methods described herein.

In yet other embodiments, the microbes to be treated are Gram-positive bacteria such as, for example, those from a genus selected from the group consisting of: *Lactobacillus, Azorhizobium, Streptococcus, Pediococcus, Photobacterium, Bacillus, Enterococcus, Staphylococcus, Clostridium, Butyrivibrio, Sphingomonas, Rhodococcus*, or *Streptomyces*. In yet other embodiments, the microbes to be treated are acid fast bacilli, e.g., from the genus *Mycobacterium*.

In still other embodiments, the microbes to be treated are, e.g., selected from a genus selected from the group consisting of: *Methanobacterium, Sulfolobus, Archaeoglobu, Rhodobacter*, or *Sinorhizobium*.

In other embodiments, the microbes to be treated are fungi, such as a fungus from the genus *Mucor* or *Candida*, e.g., *Mucor racemosus* or *Candida albicans*.

In other embodiments, the microbes to be treated are protozoa. In certain embodiments the microbe is a malaria or cryptosporidium parasite.

Routes of administration and pharmaceutical formulations such for example, therapeutic vaccines, for use in methods that induce a therapeutic immune response for treating microbial infections include those described above in connection with vaccine adjuvant administration. Dosages of the peptide, composition, and/or vaccine can be readily determined by one skilled in the art and can include broad ranges such as, for example, from about 0.05, 0.1, 0.5 or 1 milligram per kilogram subject body weight, up to about 10, 50 or 100 milligrams per kilogram subject body weight, or more.

The methods in the above described embodiments can be administered in combination or concurrently with known antimicrobial drugs, including but not limited to those described in U.S. Pat. No. 6,346,391 to Oethinger et al.

The methods and compositions described herein can be used in wound treatments. As noted above, an aspect of the disclosure provides a method of enhancing wound healing in a subject in need thereof, comprising administering (e.g., by topical administration to a wound or wound tissue) a MCAP to a subject afflicted with a wound in an amount effective to enhance healing of the wound. In addition, the disclosure provides a method of reducing scar formation in a subject in need thereof, comprising administering (e.g., by topical administration to a wound or wound tissue) a mast cell membrane activator to a subject afflicted with a wound in an amount effective to reduce scar formation during healing of said wound. Any type of surgical or traumatic wound may be treated, including wounds to the skin or skin tissue, as well as internal tissues such as muscle and connective tissues. Wound types that may be treated include wounds that are incisions, lacerations, burns, punctures, crushes, etc. Any increase in the speed or rate of wound healing is considered of benefit, and any decrease in scar tissue of clinical or cosmetic benefit is considered of benefit for purposes of this disclosure. For treating wounds the route of administration may be a topical application to the wound or wound tissue as noted above, with a topical formulation such as described above. The topical formulation may include the mast cell membrane activator in any suitable amount, such as from 1 or 2 micrograms per milliliter up to 100, 200, 500 or 1000 micrograms per milliliter, or more. The topical formulation may optionally include a permeability enhancer in any suitable amount (e.g., one to 50, 90 or 99 percent by weight), with examples of permeability enhances including but not limited to diols such as propylene glycol and glycerol; mono-alcohols such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl--2-ones (azones); any of the permeation enhancers described in, for example, U.S. Pat. No. 5,445,611, etc.

The following non-limiting examples merely provide illustration of some aspects and embodiments of the disclosure and do not limit the scope of the claims.

EXAMPLES

Example 1

Mucosal Adjuvant Activity of MCAP

To evaluate the mucosal adjuvant activity of MCAPs, C3H/HeN female mice were nasally immunized with 2.0 μg of recombinant anthrax protective antigen (rPA) either alone or in the presence of cholera toxin (CT) (1 μg; positive control adjuvant) or 20 nM of HR-1, MP, MP7 or MP17 (negative control) on days 0, 7 and 21. As shown in FIG. 1, on day 42, serum samples were collected and tested for the presence of anti-rPA serum IgG by endpoint ELISA. Despite being the “gold standard” adjuvant, CT did not significantly augment serum anti-PA IgG responses at Day +42. This is likely due to the use of very low dose (2.0 μg) of antigen (as compared to others in the field who have used doses up to 40 μg for nasal immunization with CT [Boyaka, P. N. et al. (2003) *J. Immunol.* 170(11):5636-5343]). Even with the use of this low dose of antigen, HR-1, MP and MP7 provided adjuvant activity that induced significantly increased serum anti-PA IgG geometric means titers (GMT) at Day +42. In agreement with the literature, the MP17 analog was inactive and did not provide detectable adjuvant activity (Tuichibaev, M. U. et al., (1988) *Biokhimiia* 53(2):219-226; Klinker, J. F. et al., (1994) *Biochem J.* 304(Pt 2):377-383; King, T. P. et al., (2003) *Int Arch Aller Immunol.* 131(1):25-32; Straub, S. G. et al., (1998) *Diabetes* 47(7):1053-1055; Lopez-Godinez, J. et al., (2003) *Biochemical* & Biophysical Research Communications 301 (1):13-16). Therefore, MCAPs are effective adjuvants for nasally-administered vaccines.

Example 2

Induction of Protective Antibody Responses

In addition to the measurement of anti-PA IgG antibodies by ELISA, the serum was also assessed for the ability to neutralize the macrophage toxicity of anthrax lethal toxin (Staats, H. F. et al., (2007) *Infect. Immun.* 75(11):5443-5452). As shown in FIG. 2, HR-1, MP and MP7 induced serum antibodies that neutralized anthrax lethal toxin at serum dilutions of 1:32 through 1:128 ($p=0.05$, ANOVA) while cholera toxin and MP17 did not induce lethal toxin neutralizing responses greater than those detected in mice immunized with rPA alone. These results suggest that MCAP adjuvants are superior to the gold-standard mucosal adjuvant CT for the induction of protective, toxin-neutralizing antibody responses in the serum after nasal immunization and are good candidates for use in safe and effective nasal vaccine formulations utilizing MCAP adjuvants for the induction of protective, neutralizing serum antibodies.

Next, the serum was further tested at Day +42 for the presence of antibodies specific for the peptide adjuvants. Serum IgG antibodies specific for the MCAP adjuvants were not detected in serum of mice immunized with rPA+HR-1, MP, MP7 or MP17 (data not shown). These results suggest that the lack of immunogenicity of the MCAP adjuvants will allow these adjuvants to be repeatedly used without the concern that host anti-adjuvant immune responses will decrease adjuvant effectiveness with repeated use. Indeed, others have reported that pre-existing anti-CT antibody responses decreased the ability of CT to augment antigen-specific responses, although higher doses for repeat immunizations may overcome the inhibitory effects of pre-existing anti-CT immunity (Lycke, N. et al., (1991) *Scand. J. Immunol.* 33(6): 691-698; Bergquist, C. et al., (1997) *Infection* & Immunity 65(5): 1579-1583).

Example 3

Combination Adjuvants—Induction of Protective Immunity

It has been previously reported that combinations of adjuvants used for nasally-administered vaccines induced antigen-specific antibody responses superior to those induced by individual adjuvants (Bradney, C. P. et al., (2002) *J. Virol.* 76(2):517-524). Others skilled in the art have also reported that the efficacy of the yellow fever virus vaccine was associated with its ability to provide adjuvant activity by activating multiple toll-like receptors (Querec, T. et al., (2006) *J. Exp. Med.* 203(2):413-424). Next, experiments were performed to determine whether the use of adjuvant combinations after nasal immunization with a botulinum neurotoxin subunit immunogen, HcBtre-Ad2F, would induce immune responses sufficient to protect 100% of the mice against a 20,000 $LD_{50}$ challenge while using a low antigen dose (Maddaloni, M. et al., (2006) *J. Immunol.* 177(8):5524-5532). Female BALB/c mice were nasally immunized on day 0, 7 and 14 with 20 μg HcBtre-Ad2F alone or combined with the adjuvants CT (control), CpG (TLR9 ligand), MPL (TLR4 ligand), interleukin 1α (IL-1α) or MP7 alone or in combinations of CpG+MP7, MPL+MP7 or IL-1α+MP7. As shown in Table 1 below, serum was collected on day 27 and analyzed for the presence of anti-β-tre IgG.

TABLE 1

Adjuvant Combinations Enhance the Induction of Protective Immunity After Nasal Immunization

| Group | Antigen | Adjuvant | Day 27 Anti-β-tre IgG Titer | % Survival After Day 42 20,000 LD$_{50}$ Challenge |
|---|---|---|---|---|
| 1 | HcBtre-Ad2F | None | <1:64 | 0% |
| 2 | HcBtre-Ad2F | CT | 1:49,667 [A] | 67% [F] |
| 3 | HcBtre-Ad2F | CpG (10 µg) | 1:3,104 [A] | 0% |
| 4 | HcBtre-Ad2F | MPL (10 µg) | 1:9,410 [A] | 0% |
| 5 | HcBtre-Ad2F | IL-1α (1 µg) | 1:43,237 [A] | 0% |
| 6 | HcBtre-Ad2F | MP7 (20 nmoles) | 1:14,263 [A] | 40% [F] |
| 7 | HcBtre-Ad2F | CpG + MP7 | 1:114,104 [A, B] | 100% [F] |
| 8 | HcBtre-Ad2F | MPL + MP7 | 1:228,209 [A, C, D] | 80% [F] |
| 9 | HcBtre-Ad2F | IL-1 + MP7 | 1:912,838 [A, C, E] | 100% [F] |

Female BALB/c mice (5 per group) were nasally immunized with HcBtre-Ad2F (20 µg) combined with the indicated adjuvants on days 0, 7 and 14. Serum samples were collected on day +27 and tested for the presence of anti-β-tre IgG by ELISA. On day +42 mice were challenged with 20,000 LD$_{50}$ BoNT/A and monitored for survival as we previously described[(25)]. ELISA anti-β-tre IgG titers were compared using ANOVA/Tukey multiple comparisons procedure (GraphPad Prism).
[A] significantly greater than titers induced by β-tre with no adjuvant.
[B] significantly greater than titers induced by β-tre + CpG.
[C] significantly greater than titers induced by β-tre + M7.
[D] significantly greater than titers induced by β-tre + MPL.
[E] Significantly greater than titers induced by β-tre + IL-1α.
[F] survival significantly increased compared to mice immunized with β-tre alone (Gehan-Breslow-Wilcoxon Test, GraphPad Prism).
[(25)] Maddaloni, M. et al., (2006) *J. Immunol.* 177(8): 5524-5532

All adjuvants were effective at inducing significantly increased serum anti-β-tre IgG titers. All adjuvant combinations tested increased the serum anti-β-tre IgG titers above those observed in mice immunized using individual adjuvants. At day 42, all mice were challenged by the intraperitoneal route with 20,000 LD$_{50}$ botulinum neurotoxin (Maddaloni, M. et al., (2006) *J. Immunol.* 177(8):5524-5532; Metabiologics, Madison, Wis.). As shown in Table 1 (above), of the individual adjuvants, only CT and MP7 provided measureable protection against the lethal botulinum neurotoxin challenge. CpG, MPL and IL-1α provided no protection against the 20,000 LD$_{50}$ botulinum neurotoxin A lethal challenge despite inducing increased serum antibody responses. However, when these adjuvants were combined with the MCAP adjuvant MP7 (CpG+MP7, MPL+MP7 or IL-1α+MP7), combinations of adjuvants provided 80-100% protection against the lethal challenge (see Table 1 above). Of interest was the observation that MP7 alone provided 40% survival while inducing a serum antibody titer of 1:14,263 while IL-1α induced a serum titer of 1:43,237 but provided no protection. This observation suggests that adjuvants differentially influence the induction of protective antibody responses that may not correlate with ELISA titer.

Example 4

Mast Cell Peptide Analogs with Nasal Adjuvant Activity

Next, studies were performed to determine if novel mastoparan analogs could be developed that exhibit adjuvant activity. Based on previous studies, novel cationic peptides were synthesized and tested for adjuvant activity when nasally delivered with recombinant anthrax protective antigen (rPA; 2.0 µg) to female C3H mice on days 0, 7 and 21. Mice immunized with rPA alone or rPA+CT (1 µg) served as controls. Peptides were tested at 20 nmoles per mouse, per dose and comprised the following sequences:

```
                                           (SEQ ID NO: 66)
Duke Mast C:   W-Q-W-R-W-W-W-W-W-R-R-W-W-NH2

(SEQ ID NO: 67)
Duke Mast F:   W-R-W-R-W-W-W-W-W-R-R-W-W-NH2

(SEQ ID NO: 68)
Duke Mast I:   W-Q-W-R-W-W-W-W-W-R-W-W-W-NH2
```

Figure 3:
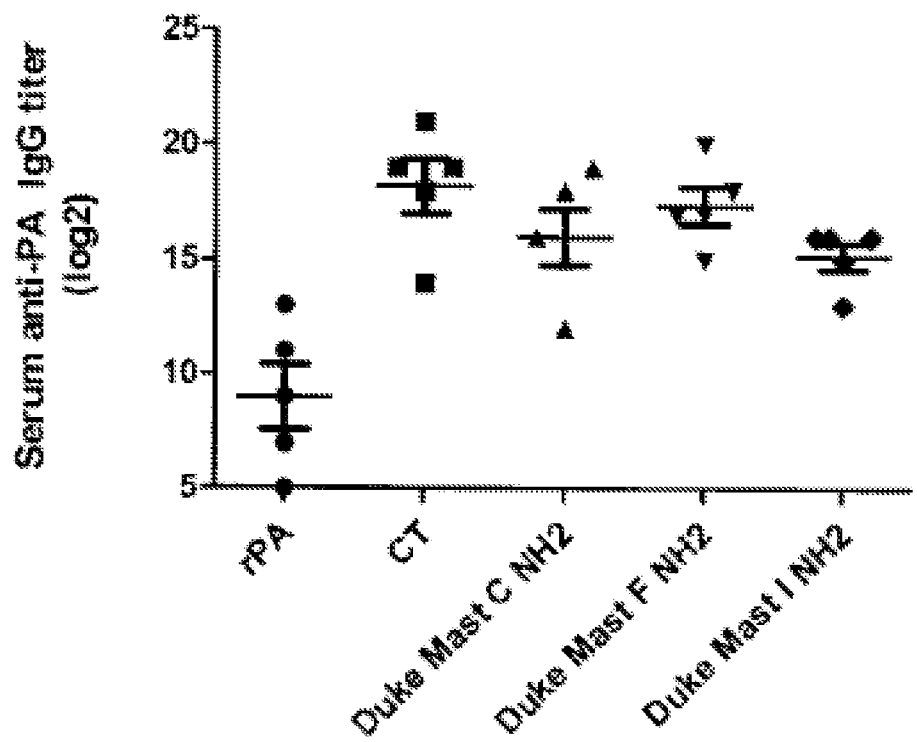
FIG. 3 depicts the effects of mastoparan analogs in a nasal vaccine composition. Female C3H mice were nasally immunized on days 0, 7 and 21. Mice were immunized with TPA alone (2.0 μg) or rPA+cholera toxin (1 μg) served as controls. Peptides were tested at 20 nmoles per mouse, per dose when combined with rPA.

On Day 28, serum samples were tested by ELISA for the presence of antigen-specific (rPA) IgG. As shown in FIG. 3 and Table 2, the novel peptides listed above (Duke Mast C, Duke Mast F and Duke Mast I) provided statistically significant adjuvant activity based on their ability to induce serum anti-rPA IgG titers that were significantly increased compared to anti-rPA IgG titers detected in mice immunized with rPA alone. All peptides induced serum anti-rPA IgG titers that were not significantly different from those induced by CT, the "gold standard" mucosal vaccine adjuvant (see FIG. 3 and Table 2). The peptides provided similar adjuvant activity since there were no significant differences in the serum antibody titers induced by the various peptide adjuvants (see Table 2). The peptides Duke Mast C, Duke Mast F and Duke Mast I provide effective adjuvant activity when delivered to a subject, such as by the nasal route with protein immunogens.

TABLE 2

Comparison of Different Mastoparan Analogs

| Tukey's Multiple Comparison Test | Significant? P < 0.05? |
|---|---|
| rPA vs CT | Yes |
| rPA vs Duke Mast C NH$_2$ | Yes |
| rPA vs Duke Mast F NH$_2$ | Yes |
| rPA vs Duke Mast I NH$_2$ | Yes |
| CT vs Duke Mast C NH$_2$ | No |
| CT vs Duke Mast F NH$_2$ | No |
| CT vs Duke Mast I NH$_2$ | No |
| Duke Mast C NH2 vs Duke Mast F NH$_2$ | No |
| Duke Mast C NH2 vs Duke Mast I NH$_2$ | No |
| Duke Mast F NH2 vs Duke Mast I NH$_2$ | No |

Example 5

Peptides Exhibiting Mast Cell Degranulating Activity

In light of the variation in mast cell degranulating activity that Mastoparan (MP), Mastoparan 7 (MP7), and Mastoparan 17 (MP17) exhibit (e.g., FIG. 1) a series of MP-based peptides containing substitutions at positions 6, 12, and 13 were generated and assessed for biological activity.

A total of 57 peptides containing single substitutions relative to MP were produced by CPC Scientific, Inc. (San Jose, Calif.) using solid-phase peptide synthesis techniques familiar in the art (Table 3). Peptide nomenclature followed an "MP-#X" convention, with # indicating the position of the substitution within the peptide chain and X indicating the single-letter code for the amino acid introduced at that position.

TABLE 3

Mastoparan analogs with amino acid substitutions at positions 6, 12 or 13

| Peptide | SEQ ID | Sequence | MW |
|---|---|---|---|
| Mastoparan | 3 | I N L K A L A A L A K K I L | 1479.9 |
| Mastoparan 7 | 4 | I N L K A L A A L A K A L L | 1422.8 |
| Mastoparan 17 | 5 | I N L K A K A A L A K K L L | 1494.9 |
| MP-12F | 6 | I N L K A L A A L A K F I L | 1498.9 |
| MP-12M | 7 | I N L K A L A A L A K M I L | 1482.9 |
| MP-12W | 8 | I N L K A L A A L A K W I L | 1537.9 |
| MP-12I | 9 | I N L K A L A A L A K I I L | 1464.9 |
| MP-12V | 10 | I N L K A L A A L A K V I L | 1450.9 |
| MP-12L | 11 | I N L K A L A A L A K L I L | 1464.9 |
| MP-12A | 12 | I N L K A L A A L A K A I L | 1422.8 |
| MP-12P | 13 | I N L K A L A A L A K P I L | 1448.9 |
| MP-12D | 14 | I N L K A L A A L A K D I L | 1466.8 |
| MP-12E | 15 | I N L K A L A A L A K E I L | 1480.8 |
| MP-12C | 16 | I N L K A L A A L A K C I L | 1454.9 |
| MP-12N | 17 | I N L K A L A A L A K N I L | 1465.8 |
| MP-12Q | 18 | I N L K A L A A L A K Q I L | 1479.9 |
| MP-12T | 19 | I N L K A L A A L A K T I L | 1452.8 |
| MP-12Y | 20 | I N L K A L A A L A K Y I L | 1514.9 |
| MP-12S | 21 | I N L K A L A A L A K S I L | 1438.8 |
| MP-12G | 22 | I N L K A L A A L A K G I L | 1408.8 |
| MP-12H | 23 | I N L K A L A A L A K H I L | 1488.9 |
| MP-12K | 24 | I N L K A L A A L A K K I L | 1479.9 |
| MP-12R | 25 | I N L K A L A A L A K R I L | 1507.9 |
| MP-13F | 26 | I N L K A L A A L A K K F L | 1513.9 |
| MP-13M | 27 | I N L K A L A A L A K K M L | 1497.9 |
| MP-13W | 28 | I N L K A L A A L A K K W L | 1553 |
| MP-13I | 29 | I N L K A L A A L A K K I L | 1479.9 |
| MP-13V | 30 | I N L K A L A A L A K K V L | 1465.9 |
| MP-13L | 31 | I N L K A L A A L A K K L L | 1479.9 |
| MP-13A | 32 | I N L K A L A A L A K K A L | 1437.8 |
| MP-13P | 33 | I N L K A L A A L A K K P L | 1463.9 |
| MP-13D | 34 | I N L K A L A A L A K K D L | 1481.8 |
| MP-13E | 35 | I N L K A L A A L A K K E L | 1495.9 |
| MP-13C | 36 | I N L K A L A A L A K K C L | 1469.9 |
| MP-13N | 37 | I N L K A L A A L A K K N L | 1480.9 |
| MP-13Q | 38 | I N L K A L A A L A K K Q L | 1494.9 |
| MP-13T | 39 | I N L K A L A A L A K K T L | 1467.9 |
| MP-13Y | 40 | I N L K A L A A L A K K Y L | 1529.9 |
| MP-13S | 41 | I N L K A L A A L A K K S L | 1453.8 |
| MP-13G | 42 | I N L K A L A A L A K K G L | 1423.8 |
| MP-13H | 43 | I N L K A L A A L A K K H L | 1503.9 |
| MP-13K | 44 | I N L K A L A A L A K K K L | 1494.9 |
| MP-13R | 45 | I N L K A L A A L A K K R L | 1522.9 |
| MP-6F | 46 | I N L K A F A A L A K K I L | 1513.9 |
| MP-6M | 47 | I N L K A M A A L A K K I L | 1497.9 |
| MP-6W | 48 | I N L K A W A A L A K K I L | 1553 |
| MP-6I | 49 | I N L K A I A A L A K K I L | 1480 |
| MP-6V | 50 | I N L K A V A A L A K K I L | 1465.9 |
| MP-6L | 51 | I N L K A L A A L A K K I L | 1479.9 |
| MP-6A | 52 | I N L K A A A A L A K K I L | 1437.8 |
| MP-6P | 53 | I N K L A P A A L A K K I L | 1463.9 |
| MP-6D | 54 | I N L K A D A A L A K K I L | 1481.8 |
| MP-6E | 55 | I N L K A E A A L A K K I L | 1495.9 |
| MP-6C | 56 | I N L K A C A A L A K K I L | 1469.9 |
| MP-6N | 57 | I N L K A N A A L A K K I L | 1480.9 |
| MP-6Q | 58 | I N L K A Q A A L A K K I L | 1494.9 |
| MP-6T | 59 | I N L K A T A A L A K K I L | 1467.9 |
| MP-6Y | 60 | I N L K A Y A A L A K K I L | 1529.9 |
| MP-6S | 61 | I N L K A S A A L A K K I L | 1453.8 |
| MP-6G | 62 | I N L K A G A A L A K K I L | 1423.8 |
| MP-6H | 63 | I N L K A H A A L A K K I L | 1503.9 |

TABLE 3-continued

Mastoparan analogs with amino acid substitutions at positions 6, 12 or 13

| Peptide | SEQ ID | Sequence | MW |
|---|---|---|---|
| MP-6K | 64 | I N L K A K A A L A K K I L | 1494.9 |
| MP-6R | 65 | I N L K A R A A L A K K I L | 1522.9 |

Peptides were tested for in vitro mast cell degranulating activity by exposing mast cells (MC/9, from American Type Culture Collection (ATCC), Manassas, Va.) to 100 μM, 20 μM, and 4 μM concentrations of each peptide and measuring subsequent β-hexosamindiase release. While the β-hexosamindiase assay can be performed as known in the art, a brief summary of the conditions used herein is provided. Peptides were added to murine MC/9 mast cells to provide the desired final peptide concentration in a final volume of 100 μl in wells of a 96-well plate. After incubation for 30 min. (at 37° C.), 30 μl of supernatant was removed and tested for the presence of β-hexosaminidase (β-hex) by combining the supernatant with the substrate p-nitrophenyl-N-acetyl-β-D-glucosaminide (NAG). Percent β-hex release was calculated by comparing β-hex released that was induced by the test material relative to a 100% release induced by treatment of MC/9 cells with Triton X-100. Peptides exhibiting stronger degranulating activity than mastoparan at 100 μM were further tested at concentrations of 80 μM, 40 μM, 10 μM, 5 μM, and 2.5 μM to allow calculation of $MCD_{10}$ and $MCD_{50}$—the concentration of each peptide necessary to induce degranulation of 10 and 50% of mast cells, respectively. $MCD_{10}$ and $MCD_{50}$ calculations were performed using GraphPad Prism. While all of the 24 peptides selected for further study exhibited in vitro mast cell degranulation activity, the activity relative to mastoparan and mastoparan 7 is summarized in Table 4.

TABLE 4

Mastoparan analogs capable of inducing mast cell degranulation

| Peptide | $MCD_{50}$ | $MCD_{10}$ |
|---|---|---|
| Mastoparan | | 33.07 |
| Mastoparan 7 | 18.1 | 6.31 |
| MP-12W | 4.71 | 1.47 |
| MP-12L | 5.19 | 2.30 |
| MP-12F | 9.22 | 4.39 |
| MP-12Y | 11.07 | 4.09 |
| MP-12M | 11.34 | 2.96 |
| MP-12I | 11.98 | 2.32 |
| MP-12C | 23.84 | 5.33 |
| MP-12A | 25.32 | 8.88 |
| MP-12V | 41.16 | 14.87 |
| MP-13C | | 17.27 |
| MP-12Q | | 18.73 |
| MP-13L | | 22.46 |
| MP-12S | | 22.50 |
| MP-13W | | 22.76 |
| MP-12R | | 23.29 |
| MP-12H | | 23.86 |
| MP-13F | | 24.37 |
| MP-6W | | 24.99 |
| MP-12N | | 31.86 |
| MP-12E | | 40.32 |
| MP-6F | | 58.40 |
| MP-6I | | 61.14 |
| MP-13M | | 64.54 |
| MP-12G | | 68.76 |

MCD50: concentration of peptide necessary to induce degranulation of 50% of mast cells;
MCD10: concentration of peptide necessary to induce degranulation of 10% of mast cells.

Example 6

Peptides Exhibiting Adjuvant Activity

Figure 5:
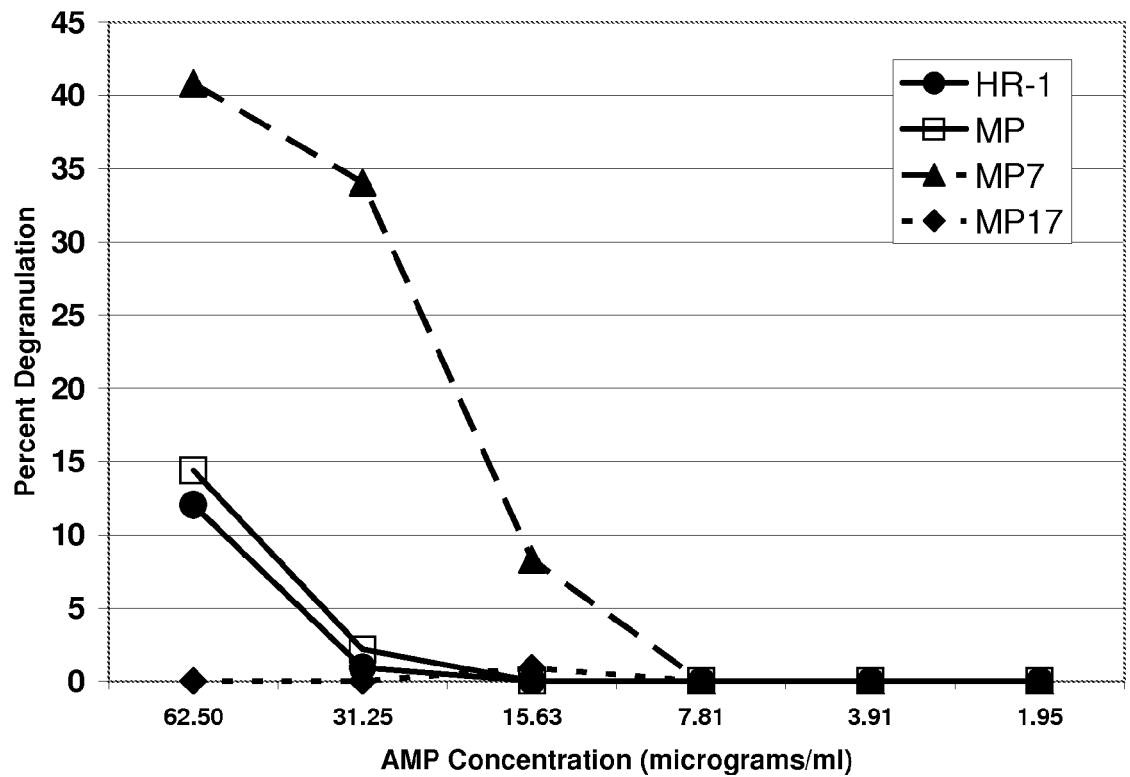
FIG. 5 depicts induction of mast cell degranulation by MCAP. Cultured MC9 cells were exposed to various concentrations of MP17 (negative control), HR-1, MP, and MP7 peptides for 30 minutes. Measurements of β-hexosaminidase, a degranulation marker, released into the culture medium revealed that HR-1, MP, and MP7 all induced mast cell degranulation.
Figure 6:
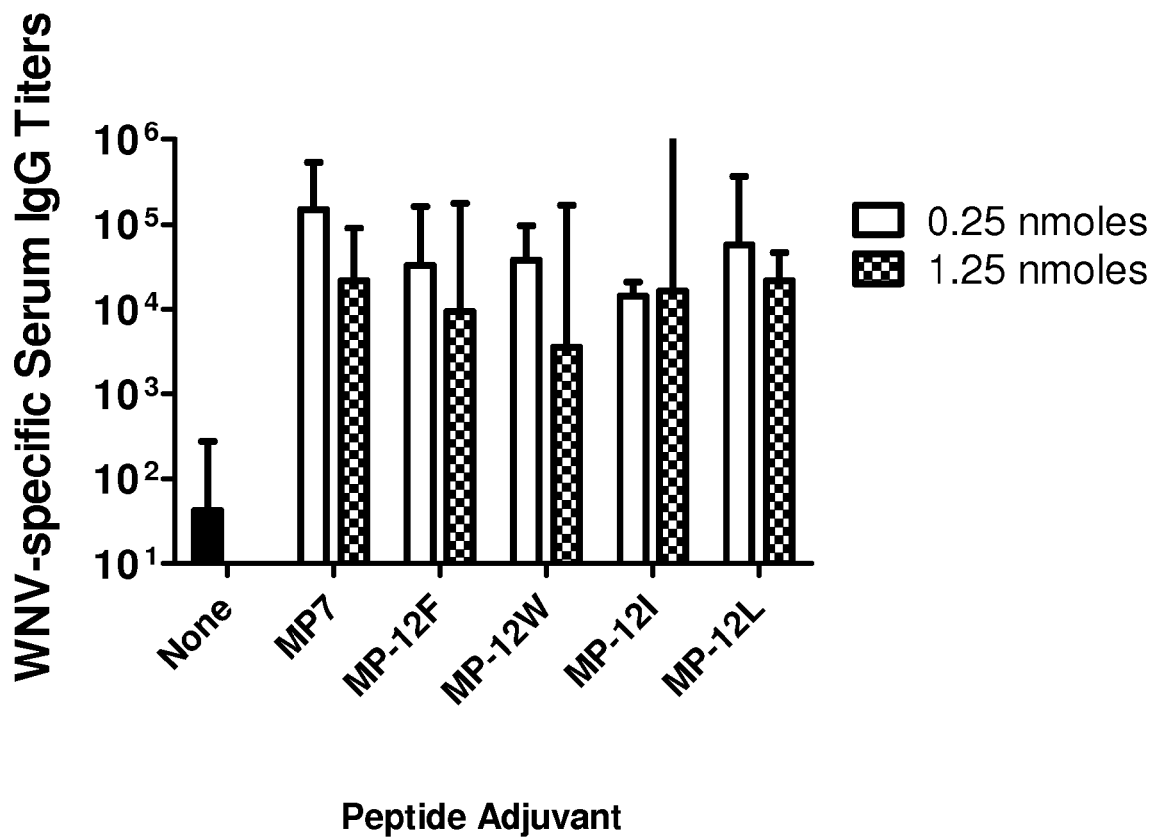
FIG. 6 depicts adjuvant activity of MCAP derived via modification of mastoparan. Female BALB/c mice were nasally immunized on days 0, 7, and 21 with West Nile Virus (WNV) antigen alone or combined with 0.25 or 1.25 nmoles the following MCAP: MP7 (positive control), MP-12F, MP-12W, MP-12I, and MP-12L. Anti-WNV IgG titers in sera on day 28 revealed adjuvant activity for each MCAP, with significantly greater (ANOVA, p<0.05) antibody responses in mice receiving antigen plus MCAP as compared to antigen alone.

MCAPs derived from MP via single amino acid substitutions and able to induce mast cell degranulation as described in the preceding example were tested for in vivo adjuvant activity. Female BALB/c mice (Charles River Laboratories, Wilmington, Mass.) were nasally immunized on days 0, 7, and 21 with 1 μg of recombinant West Nile Virus (WNV) envelope domain III trimer antigen alone or combined with MP7, MP-12W, MP-12L, MP-12F, or MP-12I peptides at 0.25 or 1.25 nmoles per immunization (Table 5). Serum samples collected from each mouse at day 28 and tested for serum anti-WNV IgG by ELISA revealed increased anti-WNV IgG titers in mice immunized with WNV antigen plus peptide than in those immunized with peptide alone (FIG. 5).

TABLE 5

Mast Cell Activating Peptides Exhibit Nasal Adjuvant Activity in Mice.

| GROUP | # OF MICE | MOUSE STRAIN | Antigen | ADJUVANT | ADJUVANT DOSE |
|---|---|---|---|---|---|
| 1 | 5 | BALB/c | WNV E Domain III (1 μg per dose) | none | None |
| 2 | 5 | | | MP7 | 1.25 nmoles |
| 3 | 5 | | | | 0.25 nmoles |
| 4 | 5 | | | MP-12F | 1.25 nmoles |
| 5 | 5 | | | | 0.25 nmoles |
| 6 | 5 | | | MP-12W | 1.25 nmoles |
| 7 | 5 | | | | 0.25 nmoles |
| 8 | 5 | | | MP-12I | 1.25 nmoles |
| 9 | 5 | | | | 0.25 nmoles |
| 10 | 5 | | | MP-12L | 1.25 nmoles |
| 11 | 5 | | | | 0.25 nmoles |

Furthermore, there was no significant difference in anti-WNV IgG titers between mice that received MP7 and those that received the peptides MP-12W, MP-12L, MP-12F, or MP-12I. Accordingly, peptides of SEQ ID NOs:1 and 2, including MP-12W, MP-12L, MP-12F, and MP-12I exhibit adjuvant activity when administered concurrently with protein antigens in vivo.

Example 7

Peptide Analogs with Mast Cell Degranulating Activity

Peptide analogs based on mastoparan and mastoparan 7 were synthesized and tested for their ability to degranulate mast cells in vitro. The amino acid sequences of these peptide analogs, as well as the results of the mast cell degranulation studies is summarized below in Table 6.

TABLE 6

Mast cell degranulating activity of mastoparan (MP) analogs

| Peptide Name | Amino Acid Sequence | SEQ ID NO | % MC/9 Degranulation | |
|---|---|---|---|---|
| | | | 20 µM | 100 µM |
| Mastoparan 17 | INLKAKAALAKKLL-OH | SEQ ID NO: 5 | not tested | 0% |
| Mastoparan | INLKALAALAKKIL-NH2 | SEQ ID NO: 3 | not tested | 66.60% |
| Mastoparan 7 | INLKALAALAKALL-NH2 | SEQ ID NO: 4 | 50.25% | 80.20% |
| Duke MCAP C | WQWRWWWWWWRRWW-NH2 | SEQ ID NO: 66 | not tested | 47.90% |
| Duke MCAP F | WRWRWWWWWWRRWW-NH2 | SEQ ID NO: 67 | 27.80% | 40.07% |
| Duke MCAP I | WQWRWWWWWWRWWW-NH2 | SEQ ID NO: 68 | not tested | 30.50% |
| MP7-2X | INLKALAALAKALLINLKALAALAKALL-NH2 | SEQ ID NO: 69 | 33.60% | 47.80% |
| MP7-2XA | INLKALAALAKALLSGGRGGINLKALAALAKALL-NH2 | SEQ ID NO: 70 | 50.20% | 78.40% |
| MP7-2XB | INLKALAALAKALLGGGINLKALAALAKALL-NH2 | SEQ ID NO: 71 | 40.49% | 56.90% |

In previous studies, all peptides with in vitro degranulating activity also exhibit in vivo adjuvant activity. Studies will be performed to evaluate the in vivo adjuvant activity of the novel mast cell activating peptides. In such experiments, female BALB/c mice (5 per group) will be nasally immunized with an immunogen, such as HcBtre-Ad2F (20 µg) combined with the indicated adjuvants from Table 3 on days 0, 7 and 14. Serum samples will be collected on Day +27 and tested for the presence of anti-β-tre IgG antibody by ELISA. On Day +42, mice will be challenged with 20,000 $LD_{50}$ BoNT/A and monitored for survival as previously described (Maddaloni, M., et al., (2006) *J. Immunol.* 177(8):5524-5532). ELISA anti-β-tre IgG titers will be compared using ANOVA/Tukey multiple comparisons procedure (GraphPad Prism).

Example 8

Effect of Terminal Amino Acid Modifications on Mast Cell Degranulating Activity In light of reported effects of terminal modifications on MP biological activity, MP7, MP-12F, MP-12I, MP-12L, and MP-12W peptides with (1) no modification, (2) C-terminal amidation, (3) N-terminal acetylation, or (4) C-terminal amidation and N-terminal acetylation were synthesized and evaluated for mast cell degranulating activity (Table 7). Peptides were produced by CPC Scientific (San Jose, Calif.). Resulting peptides were screened for activity using an in vitro degranulation assay, exposing MC/9 cells to each peptide at 100 μM. Peptides exhibiting degranulating activity were further tested at 80 μM, 40 μM, and 20 μM. All amidated peptides exhibited enhanced degranulating activity relative to their analogs with unmodified C-termini. N-terminal acetylation did not impair degranulating activity.

TABLE 7

Influence of Peptide Terminal Modifications on Mast Cell Degranulation

| Peptide | N-term | SEQ ID | Amino Acid Sequence | C-term | % Mast Cell Degranulation 100 μM | 80 μM | 40 μM | 20 μM |
|---|---|---|---|---|---|---|---|---|
| NP7-NH2 | — | SEQ ID NO: 4 | I N L K A L A A L A K A L L | NH2 | | 72.33 | 54.35 | 39.12 |
| MP7-OH | — | | I N L K A L A A L A K A L L | OH | 2.87 | | | |
| MP7-Ac | Ac | | I N L K A L A A L A K A L L | NH2 | 0.31 | | | |
| MP7-Ac-NH2 | Ac | | I N L K A L A A L A K A L L | NH2 | | 54.46 | 47.52 | 29.89 |
| MP-12F-NH2 | — | SEQ ID NO: 66 | I N L K A L A A L A K F I L | NH2 | | 95.24 | 87.57 | 70.01 |
| MP-12F-OH | — | | I N L K A L A A L A K F I L | OH | 38.07 | | | |
| MP-12F-Ac | Ac | | I N L K A L A A L A K F I L | OH | 2.75 | | | |
| MP-12F-Ac-NH2 | Ac | | I N L K A L A A L A K F I L | NH2 | | 87.65 | 83.36 | 67.41 |
| MP-12I-NH2 | — | SEQ ID NO: 9 | I N L K A L A A L A K I I L | NH2 | | 81.66 | 70.13 | 49.9 |
| MP-12I-OH | — | | I N L K A L A A L A K I I L | OH | 0 | | | |
| MP-12I-Ac | Ac | | I N L K A L A A L A K I I L | OH | 0 | | | |
| MP-12I-Ac-NH2 | Ac | | I N L K A L A A L A K I I L | NH2 | | 87.97 | 67.63 | 46.09 |
| MP-12L-NH2 | — | SEQ ID NO: 11 | I N L K A L A A L A K L I L | NH2 | | 83.36 | 67.37 | 51.29 |
| MP-12L-OH | — | | I N L K A L A A L A K L I L | OH | 21.36 | | | |
| MP-12L-Ac | Ac | | I N L K A L A A L A K L I L | OH | 1.07 | | | |
| MP-12L-Ac-NH2 | Ac | | I N L K A L A A L A K L I L | NH2 | | 80.35 | 76.49 | 58.57 |

TABLE 7-continued

Influence of Peptide Terminal Modifications on Mast Cell Degranulation

| Peptide | N-term | SEQ ID | Amino Acid Sequence | C-term | % Mast Cell Degranulation | | | |
|---|---|---|---|---|---|---|---|---|
| | | | | | 100 µM | 80 µM | 40 µM | 20 µM |
| MP-12W-NH2 | — | SEQ ID NO: 8 | I N L K A L A A L A K W I L | NH2 | | 79.87 | 85.74 | 80.05 |
| MP-12W-OH | — | | I N L K A L A A L A K W I L | OH | 23.83 | | | |
| MP-12W-Ac | Ac | | I N L K A L A A L A K W I L | OH | 38.76 | | | |
| NP-12W-Ac-NH2 | Ac | | I N L K A L A A L A K W I L | NH2 | | 82.5 | 64.75 | 41.58 |

Example 9

Peptides Exhibiting Adjuvant Activity in C-Terminal-OH or —NH₂ Form

Figure 4:
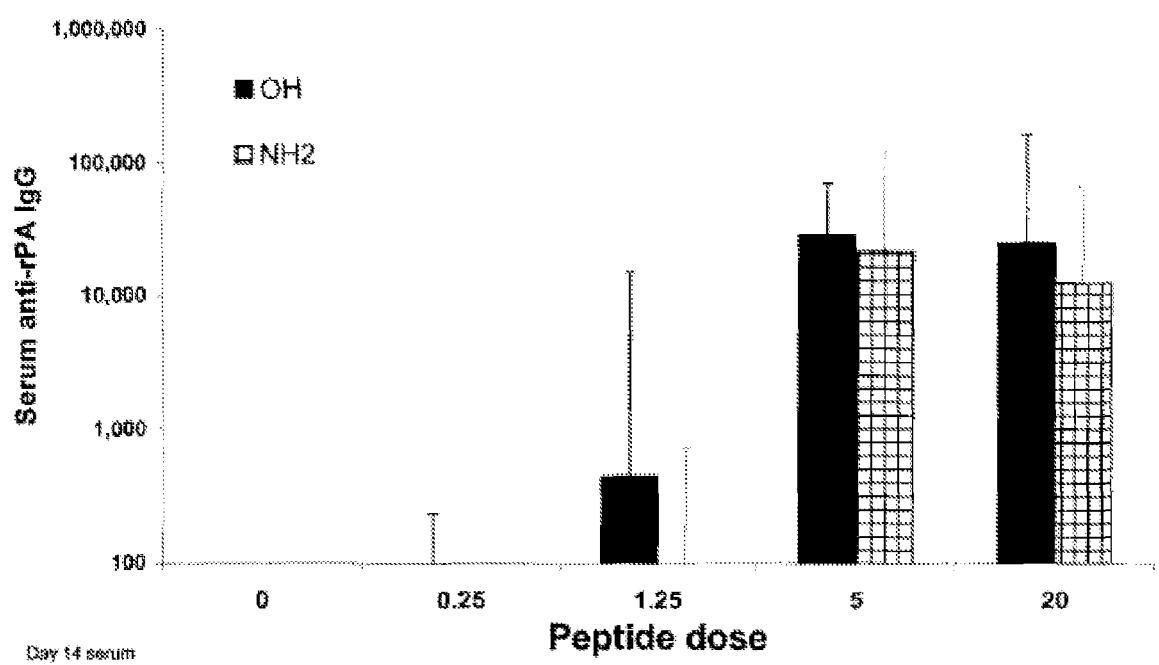
FIG. 4 depicts the effects of —OH and —NH$_2$ modifications on the C-terminal amino acid of Mastoparan 7 when administered as a nasal vaccine adjuvant.

As discussed above, peptides can be synthesized with the C-terminal amino acid in the —OH form or the —NH₂ form. To determine if the form of the C-terminal amino acid influenced the nasal adjuvant activity of mastoparan 7, female C3H/HeN mice were nasally immunized with recombinant anthrax protective antigen (rPA; 2.0 µg) alone or in combination with mastoparan 7-OH or mastoparan 7-NH₂ at 0.25, 1.25, 5 or 20 nmoles. Mice were immunized on days 0 and 7. Serum was collected on day 14 and tested for the presence of anti-rPA IgG responses by ELISA. Using ANOVA and multiple comparisons test (Tukey), and as shown in FIG. 4, there was no significant difference between the serum anti-rPA IgG titers for the —OH and —NH₂ forms at each peptide dose. However, mastoparan-NH₂ at 1.25 nmoles induced a serum IgG titer significantly greater than the IgG titer in mice immunized with rPA alone while mice immunized with the mastoparan-OH peptide at 1.25 nmoles has serum anti-PA titers that were not significantly different from mice immunized with rPA alone. Nevertheless, any peptide that is identified in the C-terminal —NH₂ form as exhibiting mast cell degranulation activity, is expected to have significant adjuvant activity in the —OH form at least as a nasal vaccine when used at an appropriate dose, which can be determined through careful dose response studies.

Example 10

Comparison of Nasal Adjuvant Activity: Mastoparan vs IC31

Adjuvant activity provided by cationic peptides can be enhanced by combination with other adjuvants such as CpG (Kindrachuk J, et al., Vaccine. 2009; 27(34):4662-71; Schellack C., et al., Vaccine. 2006; 24(26):5461-72). An adjuvant termed IC31 (Intercell AG, Vienna, Austria) combines a cationic peptide and CpG and has progressed to human clinical studies (van Dissel J T, et al., Vaccine. 2010; 28(20):3571-81). Comparative data of the mastoparan peptides described herein to IC31 when delivered intranasally show that the MCAP peptides of the disclosure provided significant adjuvant activity while the IC31 peptide did not (below). Thus, the potency of the peptides described herein may be superior to the potency of cationic peptide adjuvants used by others. Further, the required dosage of the peptide adjuvants described herein may be less than those previously known in the art. For example, the peptides described herein can provide adjuvant activity in a amounts as low as 20 nmoles (~28 µg) or less (via nasal immunization), while known peptides have used higher doses (100-900 nmoles, via s.c. injection).

Female C3H/HeN mice were nasally immunized with 2.0 µg of anthrax recombinant protective antigen (rPA) alone or combined with mastoparan-OH, mastoparan-NH2, mastoparan 17-OH, KLKLLLLLKLK-OH (IC31), KLKLLLLLKLK-NH2 (IC31), or cholera toxin (1 µg) on days 0, 7 and 21. All peptides were at 20 nmoles of peptide per vaccine dose. On day 28, serum samples were collected and tested for the presence of anti-PA IgG by ELISA. Mastoparan-OH and mastoparan-NH2 provided adjuvant activity for nasally delivered PA and induced serum anti-PA IgG titers comparable to those induced by the classic mucosal adjuvant cholera toxin (CT). Mastoparan 17-OH (a negative control peptide), KLKLLLLLKLK-OH and KLKLLLLLKLK-NH2 did not provide adjuvant activity as determined by serum anti-PA IgG endpoint titers (data not shown).

The results presented herein present several advantages over currently available technology. First, the peptide adjuvants presented herein can be produced at a very low cost, especially when scaled up to large quantities. Second, these synthetic peptides can be produced at very high purity. Third, the peptide adjuvants presented herein provide adjuvant activity via a mechanism that does not appear to utilize toll-like receptors, thereby allowing them to be combined with TLR ligand adjuvants to provide an adjuvant cocktail having adjuvant activity superior to using adjuvants individually.

The patents and publications referred to herein are incorporated by reference.

We claim:

1. An isolated peptide of Formula I:

$R_1$-$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$R_2$ (SEQ ID NO:1)

wherein
- $X_1$ is W;
- $X_2$ is N, Q, or R;
- $X_3$ is L or W;
- $X_4$ is K or R;
- $X_5$ is A or W;
- $X_6$ is any amino acid;
- $X_7$ is A or W;
- $X_8$ is A or W;
- $X_9$ is L or W;
- $X_{10}$ is A, V, or W;
- $X_{11}$ is K or R;
- $X_{12}$ is any amino acid;
- $X_{13}$ is any amino acid;
- $X_{14}$ is L or W;
- $R_1$ is absent or Ac; and
- $R_2$ is NH$_2$ or OH;

or a salt thereof.

2. An isolated peptide of Formula II:
$R_1$-I-N-L-K-A-$X_6$-A-A-L-A-K-$X_{12}$-$X_{13}$-L-$R_2$ (SEQ ID NO:2)
wherein
$X_6$ is W, L, F, or I;
$X_{12}$ is W, L, F, Y, M, I, C, V, Q, S, H, E, or G;
$X_{13}$ is C, L, W, F, or M;
$R_1$ is absent or Ac; and
$R_2$ is $NH_2$ or OH;
or a salt thereof.

3. The peptide of claim 2, wherein $X_6$ is leucine.

4. An isolated peptide of Formula II:
$R_1$-I-N-L-K-A-$X_6$-A-A-L-A-K-$X_{12}$-$X_{13}$-L-$R_2$ (SEQ ID NO:2)
wherein $X_6$ is leucine, $X_{13}$ is isoleucine, and $X_{12}$ is W, L, F, Y, M, I, C, V, Q, S, H, or E.

5. A composition comprising an immunogen in combination with at least one peptide comprising the isolated peptide of claim 1.

6. The composition according to claim 5 further comprising an additional adjuvant.

7. The composition according to claim 6, wherein the additional adjuvant is selected from the group consisting of LPS, CpG, MPL, IL-1α, IL-1β, and any combination thereof.

8. A vaccine comprising an immunogen and at least one peptide, wherein the immunogen is recombinant anthrax protective antigen and wherein the at least one peptide is selected from the group consisting of SEQ ID NO: 6, SEQ ID NO: 8, SEQ ID NO: 9, SEQ ID NO: 11, SEQ ID NO: 66, SEQ ID NO: 67, and SEQ ID NO: 68.

9. The vaccine according to claim 8 further comprising an additional adjuvant.

10. The vaccine according to claim 9, wherein the additional adjuvant is selected from the group consisting of LPS, CpG, MPL, IL-1α, IL-1β, and any combination thereof.

* * * * *